United States Patent [19]

Schmidt et al.

[11] 4,333,868
[45] Jun. 8, 1982

[54] PHOSPHITE ESTER STABILIZERS

[75] Inventors: Andreas Schmidt, Reinach; Kurt Schwarzenbach, Pfeffingen, both of Switzerland

[73] Assignee: Ciba-Geigy Corporation, Ardsley, N.Y.

[21] Appl. No.: 104,502

[22] Filed: Dec. 17, 1979

Related U.S. Application Data

[60] Continuation of Ser. No. 948,939, Oct. 6, 1978, abandoned, which is a division of Ser. No. 709,135, Jul. 27, 1976, Pat. No. 4,132,702, which is a continuation-in-part of Ser. No. 561,394, Mar. 24, 1975, abandoned.

[30] Foreign Application Priority Data

Mar. 27, 1974 [CH] Switzerland ............... 004282/74

[51] Int. Cl.³ ............... C07F 9/145; C08K 5/52
[52] U.S. Cl. ............... 524/152; 260/953
[58] Field of Search ............... 260/45.95 D, 45.8 R, 260/45.9 NP, 927 R, 937, 944, 953

[56] References Cited

U.S. PATENT DOCUMENTS

| | | | |
|---|---|---|---|
| 3,017,422 | 1/1962 | Thompson | 260/953 |
| 3,281,505 | 10/1966 | Spivack | 260/953 |
| 3,361,846 | 1/1968 | Gleim et al. | 260/953 |
| 3,763,287 | 10/1973 | Chiddix et al. | 260/953 |
| 3,795,700 | 3/1974 | Brook et al. | 260/45.85 |
| 3,925,306 | 12/1975 | Schlichting et al. | 260/45.95 |
| 3,927,091 | 12/1975 | Huber-Emden et al. | 260/45.9 |
| 3,975,360 | 8/1976 | Kline | 260/45.85 R |
| 4,067,895 | 1/1978 | Hofer et al. | 260/45.9 |
| 4,069,200 | 1/1978 | Spivack | 260/953 |
| 4,091,225 | 5/1978 | Parker | 260/45.85 |
| 4,100,191 | 7/1978 | Fischer et al. | 260/45.9 |
| 4,132,702 | 1/1979 | Schmidt et al. | 260/45.8 N |

OTHER PUBLICATIONS

CA 82, 3991c, (1975).

Primary Examiner—V. P. Hoke
Attorney, Agent, or Firm—Luther A. R. Hall

[57] ABSTRACT

Compounds of the formula I

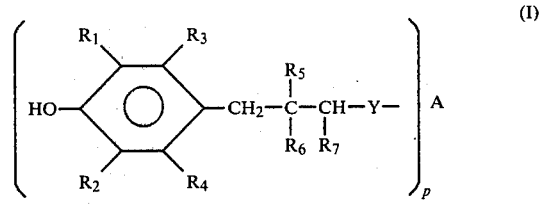

in which $R_1$ and $R_2$ independently of one another denote alkyl, cycloalkyl or aralkyl, $R_3$ denotes hydrogen or, conjointly with $R_1$, denotes tetramethylene, $R_4$ denotes hydrogen or lower alkyl or, conjointly with $R_2$, denotes tetramethylene, $R_5$ denotes hydrogen, alkyl, aralkyl, acyloxyalkyl, oxaalkyl or phenyl, $R_6$ denotes hydrogen, alkyl, phenyl or the group

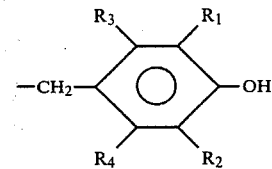

or, conjointly with $R_5$, denotes alkylene, $R_7$ denotes hydrogen, alkyl, phenyl, benzyl or alkylphenyl or, conjointly with $R_5$ or $R_6$, denotes alkylene or, conjointly with $R_5$ and $R_6$, denotes alkanetriyl, $R_5$, $R_6$ and $R_7$ together containing at least one carbon atom, Y denotes —O— or —NH—, P denotes 1, 2, 3 or 4 and A denotes hydrogen or a group which is derived from an organic or inorganic oxygen acid A-(OH)$_p$, are suitable for stabilizing organic material against thermo-oxidative degradation.

2 Claims, No Drawings

PHOSPHITE ESTER STABILIZERS

This is a Continuation of application Ser. No. 948,939, filed on Oct. 6, 1978, now abandoned; which in turn is a Divisional of application Ser. No. 709,135, filed on July 27, 1976, now U.S. Pat. No. 4,132,702, issued on Jan. 2, 1979; which in turn is a continuation-in-part of application Ser. No. 561,394, filed on Mar. 24, 1975, now abandoned.

The present invention relates to new compounds, the method of manufacturing them, their use for stabilising organic material against thermo-oxidative degradation and the organic material stabilised with their aid.

The present invention relates to new compounds of the formula I

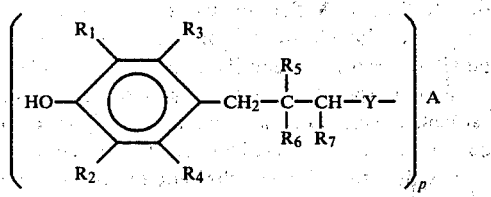

in which $R_1$ and $R_2$ independently of one another denote alkyl, cycloalkyl or aralkyl, $R_3$ denotes hydrogen or, conjointly with $R_1$, denotes tetramethylene, $R_4$ denotes hydrogen or lower alkyl or, conjointly with $R_2$, denotes tetramethylene, $R_5$ denotes hydrogen, alkyl, aralkyl, acyloxyalkyl, oxaalkyl or phenyl, $R_6$ denotes hydrogen, alkyl, phenyl or the group

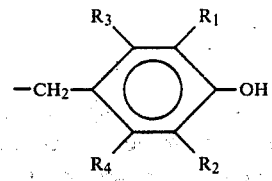

or, conjointly with $R_5$, denotes alkylene, $R_7$ denotes hydrogen, alkyl, phenyl, benzyl or alkylphenyl or, conjointly with $R_5$ or $R_6$, denotes alkylene or, conjointly with $R_5$ and $R_6$, denotes alkanetriyl, $R_5$, $R_6$ and $R_7$ together containing at least one carbon atom, Y denotes —O— or —NH—, p denotes 1, 2, 3 or 4 and A denotes hydrogen or a group which is derived from an organic or inorganic oxy-acid A-(OH)$_p$.

Preferred compounds among the compounds of the Formula I are those of the formula

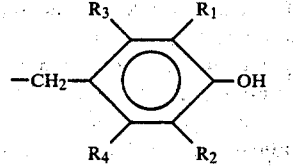

in which $R_1$ and $R_2$ independently of one another denote alkyl, cycloalkyl or aralkyl, $R_3$ denotes hydrogen or, conjointly with $R_1$, denotes tetramethylene, $R_4$ denotes hydrogen or lower alkyl or, conjointly with $R_2$, denotes tetramethylene, $R_5$ denotes alkyl, aralkyl, acyloxyalkyl, oxaalkyl or phenyl, $R_6$ denotes alkyl, phenyl or the group

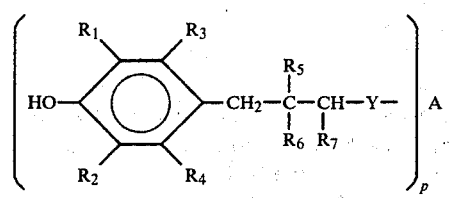

or, conjointly with $R_5$, denotes alkylene, $R_7$ denotes hydrogen, alkyl, phenyl, benzyl or alkylpenyl or, conjointly with $R_5$ or $R_6$, denotes alkylene or, conjointly with $R_5$ and $R_6$, denotes alkanetriyl, Y denotes —O— or —NH—, p denotes 1, 2, 3 or 4 and A denotes hydrogen or a group which is derived from an organic or inorganic oxy-acid A-(OH)$_p$.

It is known to employ derivatives of sterically hindered phenols at stabilisers for plastics against thermooxidative degradation or degradation induced by light.

Many of these phenol derivatives exhibit the disadvantage that they discolour the organic polymer in an objectionable manner either when they are incorporated or under the action of light or on contact with industrial flue gases or even on contact with hot water, which greatly limits their applicability in industry. New compounds have now been found which, surprisingly, are not only outstandingly suitable for stabilising organic materials, particularly organic polymers, but, in the course thereof, also remain colourless under the aforementioned conditions and protect the organic material against discolouration. This means that the new compounds stabilise the organic material both against degradation and against discolouration. Furthermore they possess good light stabilising activity.

The organic or inorganic oxygen acids of the formula A-(OH)$_p$ can be acids, the OH groups of which are linked to a carbon atom or to a hetero-atom of the radical A.

Examples of compounds of the formula I are compounds in which p and A have the following meaning:

(a) p is 1–4 and A is a radical of the formula II

$R_8$—CO— (II)

wherein, if p is equal to 1, $R_8$ denotes an aliphatic radical, a cycloaliphatic radical, an araliphatic radical, an aryl radical, an aliphatic amido radical, a heterocyclic radical, an unsubstituted or substituted amino group, an alkoxy group, a cycloalkoxy group, an aralkoxy group, an aryloxy group or a substituted mercapto group, or p is 2 and A is a group of the formula III

$$-(C-R_9)_n-CO- \quad \text{(III)}$$
$$\phantom{-(}\|\phantom{R_9)_n-CO-}$$
$$\phantom{-(}O$$

wherein n denotes O or 1 and $R_9$ denotes a direct bond or a divalent aliphatic radical, cycloaliphatic radical, aromatic radical, heterocyclic radical, aliphatic diamido radical, aliphatic diamino radical, aromatic diamino radical, aliphatic dioxy radical, cycloaliphatic dioxy radical, aromatic dioxy radical or aralkylenedioxy radical, or p is 3 and A denotes a group of the formula IV

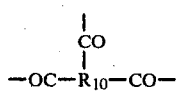
(IV)

wherein $R_{10}$ is a trivalent aliphatic radical, cycloaliphatic radical, aromatic radical, aliphatic trioxy radical, heterocyclic radical or a group of the formula V

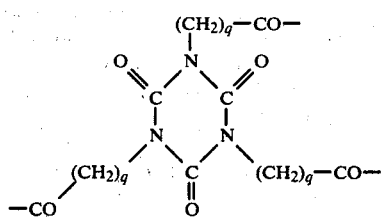
(V)

wherein q denotes 1 or 2, or p is 4 and A denotes a group of the formula VI

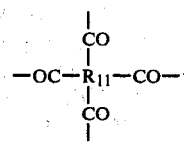
(VI)

wherein $R_{11}$ denotes a tetravalent aliphatic or aromatic radical, (b) p is 1 or 2 and A is a radical of the formula VII

(VII)

wherein p+n is equal to 2 and $R_{12}$ denotes an aliphatic radical, cycloaliphatic radical, araliphatic radical or aryl radical, an unsubstituted or substituted amino group, a heterocyclic radical, an alkoxy group, a cycloalkoxy group, an aralkoxy group, an aryloxy group or a substituted mercapto group, (c) p is 3-n-n' and A is a radical of the formula VIII

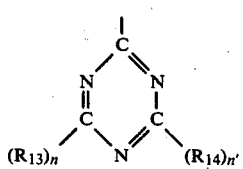
(VIII)

wherein n and n' independently of one another denote 0 or 1 and $R_{13}$ and $R_{14}$ independently of one another denote an alkoxy group, a cycloalkoxy group, an aralkoxy group, an aryloxy group, a substituted mercapto group, a substituted amino group or a radical of a heterocyclic group, (d) p is 1 and A is a radical of the formula IX

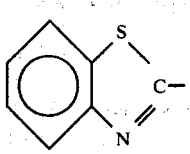
(IX)

(e) p is 3-n'-n" and A is a radical of the formula X

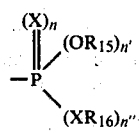
(X)

wherein n, n' and n" independently of one another denote 0 or 1, X denotes oxygen or sulphur, but only one phosphorus-sulphur bond may be contained in formula X, and $R_{15}$ and $R_{16}$ independently of one another denote hydrogen or an aliphatic radical, a cycloaliphatic radical, an araliphatic radical or an aromatic radical, or $R_{15}$ and $R_{16}$ conjointly denote a divalent aliphatic or aromatic radical, (f) p is 2-n' and A is a radical of the formula XI

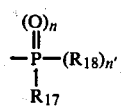
(XI)

wherein n and n' independently of one another denote 0 or 1 and $R_{17}$ denotes an aliphatic radical, a cycloaliphatic radical, an araliphatic radical or an aromatic radical, and $R_{18}$ denotes a hydroxyl group, an alkoxy group, an aryloxy group, an aliphatic radical, a cycloaliphatic radical, an araliphatic radical or an aromatic radical, (g) p is 2-m and A is a radical of the formula XII

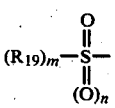
(XII)

wherein m and n independently of one another denote 0 or 1 and $R_{19}$ denotes an aromatic radical or a radical of the formula XIII

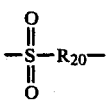
(XIII)

$R_{20}$ having the meaning of a divalent aromatic radical and being linked to the sulphur atom of the radical of the formula XIII, (h) p is 3 and A is a radical of the formulae XIV or XV

(XIV)

-continued

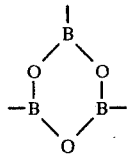
(XV)

(i) p is 4-r and A is a radical of the formula XVI

(XVI)

wherein r denotes 0 to 3 and $R_{21}$ denotes lower alkyl, and (j) p is 2 and A is a radical of the formula XVII

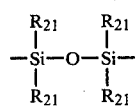
(XVII)

wherein $R_{21}$ denotes lower alkyl.

Preferred compounds among the compounds of the formula I are those in which p and A have the meaning which follows, the number of carbon atoms quoted after the radicals denoting a particular preference:

(a) p is 1 to 4 and A is a radical of the formula II

(II)

wherein, if p is equal to 1, $R_8$ denotes a straight-chain or branched alkyl group having 1–18 carbon atoms, an alkenyl group having 2–18 carbon atoms, a cycloalkyl group having 5–8 carbon atoms, an aralkyl group having 7–10 carbon atoms, an aralkyl group substituted by 1 or 2 alkyl groups which each have 1–4 carbon atoms, and/or by a hydroxyl group, a thiaalkyl group having 2–21 carbon atoms, an oxaalkyl group having 2–21 carbon atoms, a halogenoalkyl group having 2–3 carbon atoms, a hydroxyalkyl group having 1–18 carbon atoms, a dialkoxyphosphorylalkyl group having 3–10 carbon atoms, an alkoxycarbonyl group having 2–19 carbon atoms or an alkoxycarbonylalkyl group having 3–27 carbon atoms; an alkylamidoalkyl group having 3–27 carbon atoms, a dialkylamidoalkyl group having 4–25 carbon atoms, an alkylamido group having 2–19 carbon atoms, the phenyl group, a phenyl group substituted by 1 or 2 alkyl groups which each have 1–4 carbon atoms, and/or by a hydroxyl group, a phenyl group substituted by 1 to 2 chlorine atoms, an alkoxyphenyl group having 7–14 carbon atoms, an acyloxyphenyl group having 8–15 carbon atoms, a carbalkoxyphenyl group having 8–15 carbon atoms or a naphthyl group; the furyl group, the thienyl group, the pyrrolyl group, the indolyl group, the imidazolyl group, the pyrazolyl group, the 1,2,3-triazolyl group, the pyridyl group, the quinolyl group or the amino group; a straight-chain or branched alkylamino group having 1–18 carbon atoms, a straight-chain or branched dialkylamino group having 2–16 carbon atoms, the piperidyl group, the morpholinyl group, a cycloalkylamino group having 5–6 carbon atoms, an aralkylamino group having 7–14 carbon atoms, the anilino group, an anilino group substituted by 1 or 2 chlorine atoms, an alkylanilino group having 7–10 carbon atoms or a naphthylamino group; a straight-chain or branched alkoxy group having 1–18 carbon atoms, a cycloalkoxy group having 5–8 carbon atoms, an aralkoxy group having 7–14 carbon atoms, the phenoxy group, a phenoxy group substituted by 1 or 2 chlorine atoms, a phenoxy group which has 7–14 carbon atoms and which is substituted by an alkoxy group, a phenoxy group which has 7–18 carbon atoms and which is substituted by 1 to 4 alkyl groups, a naphthoxy group, a straight-chain or branched alkylthio group having 1–12 carbon atoms, a cycloalkylthio group having 5–6 carbon atoms, an aralkylthio group having 7–9 carbon atoms, the phenylthio group or a phenylthio group which has 7–14 carbon atoms and which is substituted by 1–2 alkyl groups, or p is 2 and A is a group of the formula III

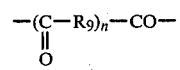
(III)

wherein n denotes 0 or 1 and $R_9$ denotes a direct bond, a straight-chain or branched alkylene group having 1–10 carbon atoms, a straight-chain or branched alkenylene group having 2–8 carbon atoms, a cycloalkylene group having 5–6 carbon atoms, an o-, m- or p-xylylene group, a thiaalkylene group having 2–4 carbon atoms, a dithiaalkylene group having 4 or 6 carbon atoms, an alkylthioalkylene group having 3–20 carbon atoms, a hydroxyalkylthioalkylene group having 4–5 carbon atoms, an acyloxyalkylthioalkylene group having 5–22 carbon atoms, an alkoxycarbonylalkylthioalkylene group having 4–22 carbon atoms, an oxaalkylene group having 2–4 carbon atoms, an alkylenediamido group having 2–6 carbon atoms, an alkylenedi(amidoalkyl) group having 4–8 carbon atoms, the piperazinediyldicarbonyl group, a phenylene group, a diphenylene group, a naphthylene group, a furanediyl group, a thiophenediyl group, a pyrazolediyl group, a 1,2,3-triazolediyl group, a pyridinediyl group, a straight-chain or branched alkylenediamino group having 2–6 carbon atoms, a straight-chain or branched N,N'-dialkylalkylenediamino group having 4–8 carbon atoms, a piperazinediyl group, a phenylenediamino group, a phenylenediamino group which has 7–10 carbon atoms and which is substituted by an alkyl group, a naphthylenediamino group, the diphenylmethane-4,4'-diamino group, a straight-chain or branched alkylenedioxy group having 2–10 carbon atoms, a cycloalkylenedioxy group having 5–6 carbon atoms, an aralkylenedioxy group having 8–10 carbon atoms or an arylenedioxy group having 6–10 carbon atoms, or p is 3 and A is a group of the formula IV

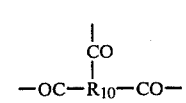
(IV)

wherein $R_{10}$ denotes an alkanetriyl group having 1–8 carbon atoms, a thiaalkanetriyl group having 2–8 carbon atoms, a cycloalkanetriyl group having 5–6 carbon atoms, a phenyltriyl group, a naphthyltriyl group, an alkanetriyltrioxy group having 3-10 carbon atoms, a pyrazoletriyl group or a pyridinetriyl group, or is a group of the formula V

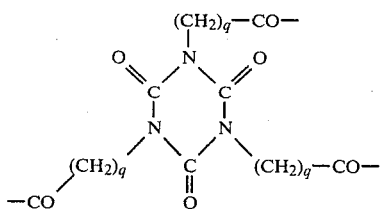

wherein q denotes 1 or 2, or p is 4 and A is a group of the formula VI

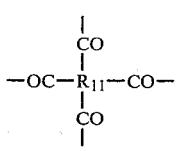

wherein $R_{11}$ denotes an alkanetetrayl group having 2-8 carbon atoms, a thiaalkanetetrayl group having 2-8 carbon atoms, a dithiaalkanetetrayl group having 6-12 carbon atoms or a phenyltetrayl group,
(b) p is 1 or 2 and A is a radical of the formula VII

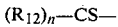
$(R_{12})_n$—CS— (VII)

wherein p+n is equal to 2 and $R_2$ denotes a straight-chain or branched alkyl group having 1-18 carbon atoms, an alkenyl group having 2-18 carbon atoms, a cycloalkyl group having 5-8 carbon atoms, an aralkyl group having 7-10 carbon atoms, the phenyl group, a phenyl group substituted by a hydroxyl group or a naphthyl group; the amino group; a straight-chain or branched alkylamino group having 1-18 carbon atoms, a straight-chain or branched dialkylamino group having 2-16 carbon atoms, the piperidyl group, the morpholinyl group, a cycloalkylamino group having 5-6 carbon atoms, an aralkylamino group having 7-14 carbon atoms, the anilino group, an alkylanilino group having 7-10 carbon atoms or a naphthylamino group; a straight-chain or branched alkoxy group having 1-18 carbon atoms, a cycloalkoxy group having 5-8 carbon atoms, an aralkoxy group having 7-14 carbon atoms, the phenoxy group, a phenoxy group substituted by 1 or 2 chlorine atoms, a phenoxy group which has 7-14 carbon atoms and which is substituted by an alkoxy group, a phenoxy group which has 7-18 carbon atoms and which is substituted by 1 to 4 alkyl groups, a naphthoxy group, a straight-chain or branched alkylthio group having 1-12 carbon atoms, a cycloalkylthio group having 5-6 carbon atoms, an aralkylthio group having 7-9 carbon atoms, the phenylthio group or a phenylthio group which has 7-14 carbon atoms and which is substituted by 1 to 2 alkyl groups.
(c) p is 3-n-n' and A is a radical of the formula VIII

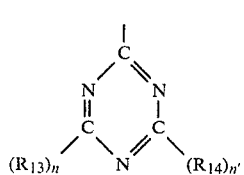

wherein n and n' independently of one another denote 0 or 1 and $R_{13}$ and $R_{14}$ independently of one another denote a straight-chain or branched alkoxy group having 1-18 carbon atoms, a cycloalkoxy group having 5-6 carbon atoms, an aralkoxy group having 7-9 carbon atoms, the phenoxy group, a phenoxy group which has 7-18 carbon atoms and which is substituted by 1-4 alkyl groups, a straight-chain or branched alkylthio group having 1-12 carbon atoms, a cycloalkylthio group having 5-6 carbon atoms, an aralkylthio group having 7-9 carbon atoms, the phenylthio group or an oranalkoxycarbonylalkylthio group having 3-21 carbon atoms; a straight-chain or branched alkylamino group having 1-18 carbon atoms, a straight-chain or branched dialkylamino group having 2-24 carbon atoms, a cycloalkylamino group having 5-6 carbon atoms, the anilino group, the piperidyl group or the morpholinyl group,
(d) p is 1 and A is a radical of the formula IX

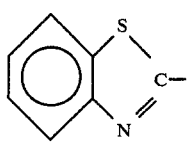

(e) p is 3-n'-n" and A is a radical of the formula X

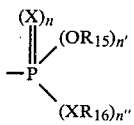

wherein n, n' and n" independently of one another denote 0 or 1, X denotes oxygen or sulphur, but only one phosphorus sulphur bond may be contained in formula X, and $R_{15}$ and $R_{16}$ independently of one another denote hydrogen, a straight-chain or branched alkyl group having 1-18 carbon atoms, a cycloalkyl group having 5-6 carbon atoms, a halogenoalkyl group having 2-3 carbon atoms, an oxaalkyl group having 2-21 carbon atoms, a thiaalkyl group having 2-21 carbon atoms, the phenyl group, an alkylphenyl group having 7-10 carbon atoms or an aralkyl group having 7-10 carbon atoms, or $R_{15}$ and $R_{16}$ conjointly denote a 1,2-alkylene group having 2-4 carbon atoms, a 1,3-alkylene group having 3-8 carbon atoms, an o-arylene group having 6-10 carbon atoms, a 1,8-naphthylene group or a group of the formula

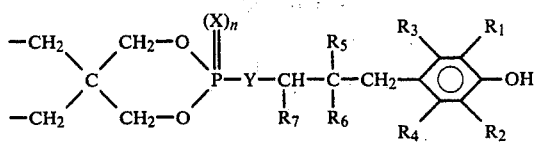

(f) p is 2-n′ and A is a radical of the formula XI

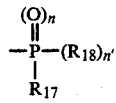

(XI)

wherein n and n′ independently of one another denote 0 or 1, $R_{17}$ denotes a straight-chain or branched alkyl group having 1-18 carbon atoms, a cycloalkyl group having 5-6 carbon atoms, the benzyl group, a benzyl group substituted by 1 or 2 alkyl groups which each have 1-5 carbon atoms, and/or by 1 hydroxyl group, or the phenyl group, and $R_{18}$ denotes the hydroxyl group, a straight-chain or branched alkoxy group having 1-18 carbon atoms, the phenoxy group, a straight-chain or branched alkyl group having 1-18 carbon atoms, a cycloalkyl group having 5-6 carbon atoms, the benzyl group or the phenyl group, (g) p is 2-m and A is a radical of the formula XII

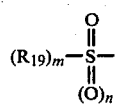

(XII)

wherein m and n independently of one another denote 0 or 1, and $R_{19}$ denotes the phenyl group, a phenyl group which has 7-12 carbon atoms and which is substituted by 1 to 4 alkyl groups, a phenyl group substituted by a halogen atom, or an α-naphthyl or β-naphthyl group, or, if n is 1, also a group of the formula XIII

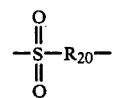

(XIII)

$R_{20}$ having the meaning of phenylene, phenylene which has 7-10 carbon atoms and which is substituted by 1 to 2 alkyl groups, or naphthylene, and $R_{20}$ being linked to the sulphur atom of the radical of the formula XIII, (h) p is 3 and A is a radical of the formulae XIV or XV $$-\overset{|}{B}-$$ (XIV)

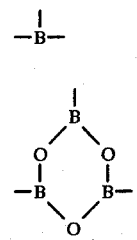

(XV)

(i) p is 4-r and A is a radical of the formula XVI

wherein r denotes 0 to 3 and $R_{21}$ denotes lower alkyl having 1-3 carbon atoms, and (j) p is 2 and A is a radical of the formula XVII $$-\underset{\underset{R_{21}}{|}}{\overset{\overset{R_{21}}{|}}{Si}}-O-\underset{\underset{R_{21}}{|}}{\overset{\overset{R_{21}}{|}}{Si}}-$$ (XVII)

wherein $R_{21}$ denotes lower alkyl having 1-3 carbon atoms.

The radicals in the abovementioned substituents $R_1$ to $R_{21}$ have, for example, the following meaning:

Alkyl in $R_1$, $R_2$, $R_5$ to $R_8$, $R_{12}$ and $R_{15}$ to $R_{18}$: methyl, ethyl, n-propyl, iso-propyl, n-butyl, sec.butyl, tert.butyl, n-amyl, sec.amyl, hexyl, octyl, decyl, dodecyl, tetradecyl, hexadecyl or octadecyl.

Lower alkyl in $R_4$ and $R_{21}$: methyl, ethyl, isopropyl, n-propyl, n-butyl, sec.butyl, tert.butyl, n-amyl, tert.amyl, sec.amyl or hexyl.

Alkyl as a substituent of a group such as phenyl, benzyl, anilino, phenoxy, phenylthio, phenylene or phenylenediamino in $R_7$ to $R_9$, $R_{12}$ to $R_{17}$ and $R_{19}$ to $R_{20}$: methyl, ethyl, n-propyl, iso-propyl, n-butyl or tert.butyl. Cycloalkyl in $R_1$, $R_2$, $R_8$, $R_9$, $R_{12}$ and $R_{15}$ to $R_{18}$: cyclohexyl, α-methylcyclohexyl or cyclooctyl.

Aralkyl in $R_1$, $R_2$, $R_5$, $R_8$, $R_{12}$, $R_{15}$ and $R_{16}$: benzyl, α-phenylethyl, α,α-dimethylbenzyl or 2-phenylpropyl.

Alkenyl in $R_8$ and $R_{12}$: propenyl, butenyl, pentenyl, hexenyl, octenyl, decenyl, tetradecenyl, octadecenyl or vinyl.

Alkoxy in $R_8$, $R_{12}$ to $R_{14}$ and $R_{18}$: methoxy, ethoxy, propoxy, n-butoxy, sec.butoxy, tert.butoxy, pentyloxy, hexyloxy, octyloxy, decyloxy, dodecyloxy or octadecyloxy.

Alkoxy as a substituent of phenoxy in $R_8$ and $R_{12}$: methoxy, ethoxy, propoxy, butoxy or octyloxy.

Cycloalkoxy in $R_8$ and $R_{12}$ to $R_{14}$: cyclohexyloxy or cyclooctyloxy.

Aralkoxy in $R_8$ and $R_{12}$ to $R_{14}$: benzyloxy or 2-phenylethoxy.

Alkylthio in $R_8$ and $R_{12}$ to $R_{14}$: methylthio, butylthio, octylthio, dodecylthio, octadecylthio or tert.octylthio.

Cycloalkylthio in $R_8$ and $R_{12}$ to $R_{14}$: cyclohexylthio.

Aralkylthio in $R_8$ and $R_{12}$ to $R_{14}$: benzylthio.

Alkoxycarbonylalkylthio in $R_{13}$ and $R_{14}$: ethoxycarbonylmethylthio, ethoxycarbonylethylthio, isooctoxycarbonylmethylthio, isooctoxycarbonylethylthio, butoxycarbonylmethylthio, octadecyloxycarbonylmethylthio or octadecyloxycarbonylethylthio.

Acyloxyalkyl in $R_5$: "acyl" can be a radical of an aliphatic or aromatic carboxylic acid having 2–18 carbon atoms, for example an alkanoic acid, such as acetic acid, propionic acid, caproic acid, lauric acid or stearic acid or an unsubstituted or substituted benzoic acid, such as benzoic acid, p-tert.butylbenzoic acid or p-tert.octylbenzoic acid. Acyloxyalkyl is, for example, 2-acetoxyethyl, 2-propionyloxyethyl, 2-caproyloxyethyl, 2-lauryloxyethyl, 2-stearyloxyethyl, 3-acetoxypropyl, 3-propionyloxypropyl, 3-lauryloxypropyl, 3-caproyloxypropyl, 3-stearyloxypropyl, benzoyloxyethyl or 3-benzoyloxypropyl.

Oxaalkyl in $R_5$, $R_8$, $R_{15}$ and $R_{16}$: 2-oxapropyl, 3-oxabutyl, 3-oxapentyl, 3-oxaheptyl, 3-oxapentadecyl or 3-oxaheneicosyl.

Thiaalkyl in $R_8$, $R_{15}$ and $R_{16}$: 3-thiabutyl, 3-thiapentyl, 3-thiaheptyl, 3-thiaundecyl, 3-thiapentadecyl, 3-thianonadecyl and 3-thiaheneicosyl.

Halogenoalkyl in $R_8$, $R_{15}$ and $R_{16}$: chloroalkyl or bromoalkyl, such as 2-chloroethyl, 2-bromoethyl or 3-chlorobutyl.

Hydroxyalkyl in $R_8$: 2-hydroxyethyl, 3-hydroxypropyl, 12-hydroxyundecyl or 18-hydroxyoctadecyl.

Dialkoxyphosphorylalkyl in $R_8$: diethoxyphosphorylethyl or dibutoxyphosphorylethyl.

Alkoxycarbonyl in $R_8$: methoxycarbonyl, ethoxycarbonyl, propoxycarbonyl, butoxycarbonyl or hexyloxycarbonyl.

Alkoxycarbonylalkyl in $R_8$: methoxycarbonylmethyl, sec.butoxycarbonylethyl, 2-ethylhexoxycarbonylbutyl, dodecyloxycarbonylbutyl, octadecyloxycarbonylhexyl, methoxycarbonylethyl, butoxycarbonyloctyl and dodecyloxycarbonyloctyl.

Alkylaminoalkyl in $R_8$: ethylamidobutyl.
Dialkylamidoalkyl in $R_8$: diethylamidoethyl.
Alkylamido in $R_8$: ethylamido.

Acyloxyphenyl in $R_8$: acetoxyphenyl, butyroyloxyphenyl, lauroyloxyphenyl or stearoyloxyphenyl.

Carbalkoxyphenyl in $R_8$: carbomethoxyphenyl or carbethoxyphenyl.

Alkylamino in $R_8$ and $R_{12}$ to $R_{14}$: methylamino, butylamino, dodecylamino or octadecylamino.

Dialkylamino in $R_8$ and $R_{12}$ to $R_{14}$: dimethylamino, diethylamino, dibutylamino or dioctylamino.

Cycloalkylamino in $R_8$ and $R_{12}$ to $R_{14}$: cyclohexylamino.

Aralkylamino in $R_8$ and $R_{12}$: benzylamino.

Halogen as a substituent of the phenyl group: chlorine or bromine.

Alkylene in $R_5+R_6$, $R_5+R_7$, $R_6+R_7$ and $R_9$: ethylene, propylene, trimethylene, tetramethylene, hexamethylene, octamethylene, decamethylene or octadecamethylene.

1,2-Alkylene in $R_{15}+R_{16}$: ethylene or 1,2-propylene.
1,3-Alkylene in $R_{15}+R_{16}$: 2,2-dimethyl-1,3-propylene, 1-methylene-1,3-propylene or 1-propylene-2-ethylene-1,3-propylene.

Cycloalkylene in $R_9$: 1,2-cyclohexylene, 1,3-cyclohexylene or 1,4-cyclohexylene.

o-Arylene in $R_{15}+R_{16}$: o-phenylene or 2,3-naphthylene.

Alkenylene in $R_9$: butenylene, pentenylene, hexenylene, octenylene, decenylene, tetradecenylene or octadecenylene.

Thiaalkylene in $R_9$: the divalent radical of 3-thiapentane, 3-thiaheptane, 3-thiaundecane, 3-thiapentadecane, 3-thianonadecane, 3-thiaheneicosane or 4-thiadecane.

Dithiaalkylene in $R_9$: —CH$_2$CH$_2$SCH$_2$CH$_2$SCH$_2$CH$_2$— or —CH$_2$CH$_2$CH$_2$SCH$_2$CH$_2$CH$_2$SCH$_2$CH$_2$—.

Alkylthioalkylene in $R_9$: ethylthioethylene, octylthioethylene or octadecylthioethylene.

Hydroxyalkylthioalkylene in $R_9$:

$$HOCH_2CH_2S\overset{|}{C}HCH_2- \text{ or } HOCH_2CH_2CH_2S\overset{|}{C}HCH_2-.$$

Acyloxyalkylthioalkylene in $R_9$:

$$CH_3COOCH_2CH_2S\overset{|}{C}HCH_2-,$$

-continued $$C_{11}H_{23}COOCH_2CH_2S\overset{|}{C}HCH_2- \text{ or }$$

$$C_{17}H_{35}COOCH_2CH_2S\overset{|}{C}HCH_2-.$$

Alkoxycarbonylalkylthioalkylene in $R_9$:

$$C_{18}H_{37}OCOCH_2S\overset{|}{C}HCH_2- \text{ or } C_2H_5OCOCH_2S\overset{|}{C}HCH_2-.$$

Oxaalkylene in $R_9$: the divalent radical of 3-oxapentane, 3-oxaheptane, 3-oxaundecane, 3-oxapentadecane or 3-oxaheneicosane.

Alkylenediamido in $R_9$: tetramethylenediamido or hexamethylenediamido.

Alkylenedi(amidoalkyl) in $R_9$: hexamethylenedi(amidomethyl).

Alkylenediamino in $R_9$: hexamethylenediamino, 2,2,4-trimethylhexamethylenediamino.

Dialkylalkylenediamino in $R_9$: N,N-dimethylhexamethylenediamino. Alkylenedioxy in $R_9$: tetramethylenedioxy or hexamethylenedioxy.

Cycloalkylenedioxy in $R_9$: 1,4-cyclohexylenedioxy.
Aralkylenedioxy in $R_9$: 1,4-xylylenedioxy.
Arylenedioxy in $R_9$: 1,3-phenylenedioxy or 1,4-phenylenedioxy.

Alkanetriyl in $R_5+R_6+R_7$ and $R_{10}$:

$$-CH_2-\overset{|}{C}H-CH_2-,\ CH_3-\overset{\overset{CH_2-}{|}}{\underset{\underset{CH_2-}{|}}{C}}-CH_2-,\ C_2H_5-\overset{\overset{CH_2-}{|}}{\underset{\underset{CH_2-}{|}}{C}}-CH_2-\text{ or}$$

$$-(CH_2)_4-\overset{|}{C}H-(CH_2)_3-$$

Thiaalkanetriyl in $R_{10}$:

$$-CH_2-S-\overset{\diagup}{\underset{\underset{\diagdown}{\overset{|}{CH_2}}}{CH}}$$

Cycloalkanetriyl in $R_{10}$: 1,3,5-cyclohexyltriyl or 1,2,4-cyclohexyltriyl.

Thiaalkanetetrayl in $R_{11}$:

$$\overset{|}{C}H_2-\overset{|}{C}H-S-\overset{|}{C}H-\overset{|}{C}H_2$$

Dithiaalkanetetrayl in $R_{11}$:

$$-CH_2\overset{|}{C}HSCH_2CH_2S\overset{|}{C}HCH_2- \text{ or}$$

$$-CH_2\overset{|}{C}HSCH_2CH_2CH_2S\overset{|}{C}HCH_2-.$$

Alkanetetrayl in $R_{11}$:

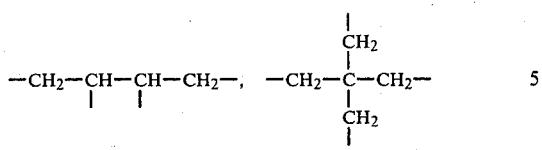

Among the particularly preferred compounds, the following groups, listed under 1 to 4, are a preferred selection:

(1) Compounds of the formula I in which $R_1$ and $R_2$ independently of one another denote alkyl having 1-8 carbon atoms, cycloalkyl having 6-8 carbon atoms, or aralkyl having 7-9 carbon atoms, $R_3$ denotes hydrogen or, conjointly with $R_1$, denotes tetramethylene, $R_4$ denotes hydrogen or methyl or, conjointly with $R_2$, denotes tetramethylene, $R_5$ denotes alkyl having 1-10 carbon atoms, aralkyl having 7-9 carbon atoms, acyloxyalkyl having 4-8 carbon atoms, oxaalkyl having 2-3 carbon atoms, or phenyl, $R_6$ denotes alkyl having 1-6 carbon atoms, phenyl or the group

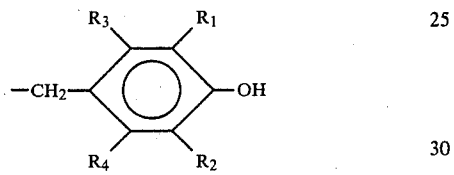

or, conjointly with $R_5$, denotes alkylene having 2-11 carbon atoms, $R_7$ denotes hydrogen, alkyl having 1-17 carbon atoms, phenyl, benzyl, alkylphenyl having 7-14 carbon atoms, or, conjointly with $R_5$ or $R_6$, denotes alkylene having 3-4 carbon atoms, or, conjointly with $R_5$ and $R_6$, denotes alkanetriyl having 5-8 carbon atoms, Y denotes —O— or —NH—, p denotes 1, 2, 3 or 4, and p and A have the following meaning:

(a) p is 1 to 4 and A is a radical of the formula II $$R_8\text{---CO---} \quad (II)$$

wherein, if p is equal to 1, $R_8$ denotes a straight-chain or branched alkyl group having 1-18 carbon atoms, an alkenyl group having 2-18 carbon atoms, a cycloalkyl group having 5-6 carbon atoms, an aralkyl group having 7-10 carbon atoms, an aralkyl group substituted by 1 or 2 alkyl groups which each have 1-4 carbon atoms, and/or by a hydroxyl group, a thiaalkyl group having 2-21 carbon atoms, a halogenoalkyl group having 2-3 carbon atoms, a dialkoxyphosphorylalkyl group having 3-6 carbon atoms, an alkoxycarbonyl group having 2-3 carbon atoms, an alkylamido group having 2-5 carbon atoms, the phenyl group, a phenyl group which is substituted by 1 or 2 alkyl groups which each have 1-4 carbon atoms, and/or by a hydroxyl group, a phenyl group substituted by 1 to 2 chlorine atoms, an alkoxyphenyl group having 7-14 carbon atoms, an acyloxyphenyl group having 8-15 carbon atoms or a naphthyl group; the furyl group, the thienyl group, the pyridyl group or the amino group; a straight-chain or branched alkylamino group having 1-18 carbon atoms, a straight-chain or branched dialkylamino group having 2-16 carbon atoms, the piperidyl group, the morpholinyl group, a cycloalkylamino group having 5-6 carbon atoms, an aralkylamino group having 7-8 carbon atoms, the anilino group, an alkylanilino group having 7-10 carbon atoms, a straight-chain or branched alkoxy group having 1-18 carbon atoms, a cycloalkoxy group having 5-8 carbon atoms, an aralkoxy group having 7-8 carbon atoms, the phenoxy group, a phenoxy group which has 7-8 carbon atoms and which is substituted by an alkoxy group, a phenoxy group which has 7-14 carbon atoms and which is substituted by 1 to 2 alkyl groups, a naphthoxy group, a straight-chain or branched alkylthio group having 1-12 carbon atoms, a cycloalkylthio group having 5-6 carbon atoms or the phenyl group, or p is 2 and A is a group of the formula III

wherein n denotes 0 or 1 and $R_9$ denotes a direct bond, a straight-chain or branched alkylene group having 1-10 carbon atoms, the ethylene group, a cycloalkylene group having 5-6 carbon atoms, a thiaalkylene group having 2-4 carbon atoms, a dithiaalkylene group having 4 or 6 carbon atoms, an alkylthioalkylene group having 3-20 carbon atoms, an alkoxycarbonylalkylthioalkylene group having 4-22 carbon atoms, the piperazinediyldicarbonyl group, a phenylene group, a naphthylene group, a straight-chain or branched alkylenediamino group having 2-6 carbon atoms, a piperazinediyl group, a phenylenediamino group which has 7-8 carbon atoms and which is substituted by an alkyl group, the diphenylmethane-4,4'-diamino group, a straight-chain or branched alkylenedioxy group having 2-10 carbon atoms, a cycloalkylenedioxy group having 5-6 carbon atoms or an arylenedioxy group having 6-10 carbon atoms, or p is 3 and A is a group of the formula IV

wherein $R_{10}$ denotes an alkanetriyl group having 1-8 carbon atoms, a thiaalkanetriyl group having 2-8 carbon atoms, a cycloalkanetriyl group having 5-6 carbon atoms, a phenyltriyl group or a naphthyltriyl group, or p is 4 and A is a group of the formula VI

wherein $R_{11}$ denotes an alkanetetrayl group having 2-8 carbon atoms, or a thiaalkanetetrayl group having 2-8 carbon atoms, (b) p is 1 or 2 and A is a radical of the formula VII $(R_{12})_n$—CS— (VII)

wherein p+n is equal to 2 and $R_{12}$ denotes a straight-chain or branched alkyl group having 1-18 carbon atoms, a cycloalkyl group having 5-8 carbon atoms, an aralkyl group having 7-10 carbon atoms, the phenyl group or an amino group; a straight-chain or branched alkylamino group having 1-8 carbon atoms, a straight-chain or branched dialkylamino group having 2-8 carbon atoms, the piperidyl group, the morpholinyl group, a cycloalkylamino group having 5-6 carbon atoms, an aralkylamino group having 7 to 14 carbon atoms, the anilino group, a straight-chain or branched alkoxy group having 1-18 carbon atoms, a cycloalkoxy group having 5-8 carbon atoms, an aralkoxy group having 7-14 carbon atoms, the phenoxy group, a phenoxy group which has 7-14 carbon atoms and which is substituted by an alkoxy group, a phenoxy group which has 7-14 carbon atoms and which is substituted by 1 to 2 alkyl groups, a straight-chain or branched alkylthio group having 1-12 carbon atoms, a cycloalkylthio group having 5-6 carbon atoms, an aralkylthio group having 7-9 carbon atoms, or the phenylthio group, (c) p is 3-n-n' and A is a radical of the formula (VIII)

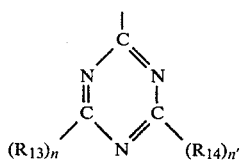

(VIII)

wherein n and n' independently of one another denote 0 or 1, and $R_{13}$ and $R_{14}$ independently of one another denote a straight-chain or branched alkoxy group having 1-12 carbon atoms, a cycloalkoxy group having 5-6 carbon atoms, an aralkoxy group having 7-9 carbon atoms, the phenoxy group, a phenoxy group which has 7-14 carbon atoms and which is substituted by 1-2 alkyl groups, a straight-chain or branched alkylthio group having 1-12 carbon atoms, a cycloalkylthio group having 5-6 carbon atoms, the phenylthio group or an alkoxycarbonylalkylthio group having 3-21 carbon atoms; a straight-chain or branched alkylamino group having 1-8 carbon atoms, a straight-chain or branched dialkylamino group having 2-16 carbon atoms, a cycloalkylamino group having 5-6 carbon atoms, the anilino group, the piperidyl group or the morpholinyl group, (d) p is 1 and A is a radical of the formula IX

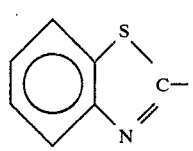

(IX)

(e) p is 3-n'-n" and A is a radical of the formula X

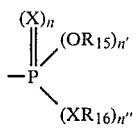

(X)

wherein n, n' and n" independently of one another denote 0 or 1, X denotes oxygen or sulphur, but only one phosphorus sulphur bond may be contained in formula X, and $R_{15}$ and $R_{16}$ independently of one another denote hydrogen, a straight-chain or branched alkyl group having 1-18 carbon atoms, a cycloalkyl group having 5-6 carbon atoms, the phenyl group or an alkylphenyl group having 7-10 carbon atoms, $R_{15}$ and $R_{16}$ conjointly denote a 1,2-alkylene group having 2-4 carbon atoms, a 1,3-alkylene group having 3-5 carbon atoms, o-phenylene or a group of the formula

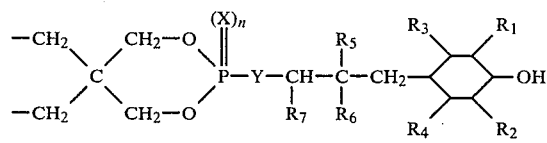

(f) p is 2-n' and A is a radical of the formula XI

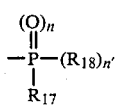

(XI)

$R_{17}$ denotes a straight-chain or branched alkyl group having 1-6 carbon atoms, a cycloalkyl group having 5-6 carbon atoms, the benzyl group, a benzyl group substituted by 1 or 2 alkyl groups which each have 1-5 carbon atoms, and/or by a hydroxyl group, or the phenyl group, and $R_{18}$ denotes the hydroxyl group, a straight-chain or branched alkoxy group having 1-18 carbon atoms, the phenoxy group, a straight-chain or branched alkyl group having 1-6 carbon atoms, a cycloalkyl group having 5-6 carbon atoms, the benzyl group or the phenyl group, (g) p is 2-m and A is a radical of the formula XII

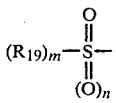

(XII)

wherein m and n independently of one another denote 0 or 1, and $R_{19}$ denotes the phenyl group, the p-tolyl group, an α-naphthyl or β-naphthyl group, or, if n is 1, also a group of the formula XIII

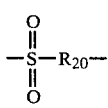

(XIII)

$R_{20}$ denoting phenylene, phenylene which has 7-10 carbon atoms and which is substituted by 1 to 2 alkyl groups, or naphthylene, and $R_{20}$ being linked to the sulphur atoms of the radical of the formula XIII, (h) p is 4-r and A is a radical of the formula XVI $$(R_{21})_r Si—  \quad (XVI)$$

wherein r denotes 0 to 3, and $R_{21}$ denotes lower alkyl having 1–3 carbon atoms.

(2) Compounds of the formula I in which $R_1$ and $R_2$ independently of one another denote alkyl having 1–4 carbon atoms, $R_3$ denotes hydrogen, $R_4$ denotes hydrogen or methyl, $R_5$ denotes alkyl having 1–4 carbon atoms, $R_6$ denotes alkyl having 1–4 carbon atoms or the group

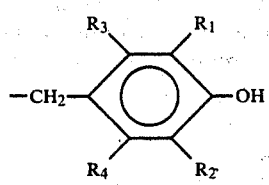

or $R_6$, conjointly with $R_5$, denotes alkylene having 4–5 carbon atoms, $R_7$ denotes hydrogen, Y denotes —O— or —NH—, p denotes 1, 2, 3 or 4, and p and A have the following meaning:

(a) p is 1 to 4 and A is a radical of the formula II $$R_8—CO— \quad (II)$$

wherein, if p is equal to 1, $R_8$ denotes a straight-chain or branched alkyl group having 1–18 carbon atoms, an alkenyl group having 2–3 carbon atoms, the cyclohexyl group, an aralkyl group having 7–10 carbon atoms, an aralkyl group substituted by 1 or 2 alkyl groups which each have 1–4 carbon atoms, and/or by a hydroxyl group, a thiaalkyl group having 2–21 carbon atoms, the phenyl group, a phenyl group substituted by 1 or 2 alkyl groups which each have 1–4 carbon atoms, and/or by a hydroxyl group, an alkoxyphenyl group having 7–11 carbon atoms, an acyloxyphenyl group having 8 carbon atoms, a naphthyl group; a straight-chain or branched alkylamino group having 1–4 carbon atoms, a straight-chain or branched dialkylamino group having 2–8 carbon atoms, the anilino group, an alkylanilino group having 7–8 carbon atoms, a straight-chain or branched alkoxy group having 1–18 carbon atoms, a cycloalkoxy group having 5–8 carbon atoms, the benzyloxy group, the phenoxy group, a phenoxy group which has 7–14 carbon atoms and which is substituted by 1 to 2 alkyl groups, or a naphthoxy group, or p is 2 and A is a group of the formula III $$-(C—R_9)_n—CO— \quad (III)$$
$$\phantom{-(}\|\phantom{R_9)_n—CO—}$$
$$\phantom{-(}O$$

wherein n denotes 0 or 1, and $R_9$ denotes a direct bond, a straight-chain or branched alkylene group having 1–8 carbon atoms, a thiaalkylene group having 2–4 carbon atoms, an alkylthioalkylene group having 3–20 carbon atoms, the piperazinediyldicarbonyl group, a phenylene group, a naphthylene group, a straight-chain or branched alkylenediamino group having 2–6 carbon atoms, a phenylenediamino group substituted by a methyl group, the diphenylmethane-4,4'-diamino group, a straight-chain or branched alkylenedioxy group having 2–6 carbon atoms, a cycloalkylenedioxy group having 5–6 carbon atoms, or an arylenedioxy group having 6–10 carbon atoms, or p is 3 and A is a group of the formula IV

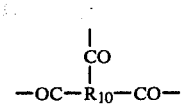

wherein $R_{10}$ denotes an alkanetriyl group having 1–8 carbon atoms, or a phenyltriyl group, or p is 4 and A is a group of the formula VI

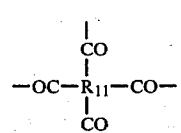

wherein $R_{11}$ denotes an alkanetetrayl group having 2–8 carbon atoms, (c) p is 3-n-n' and A is a radical of the formula VIII

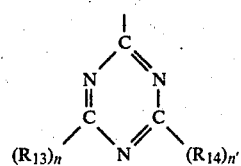

wherein n and n' independently of one another denote 0 or 1, and $R_{13}$ and $R_{14}$ independently of one another denote a straight-chain or branched alkoxy group having 1–12 carbon atoms, cyclohexyl, the phenoxy group, a straight-chain or branched alkylthio group having 1–12 carbon atoms, the phenylthio group, an alkoxycarbonylalkylthio group having 3–10 carbon atoms, a straight-chain or branched alkylamino group having 1–8 carbon atoms, a straight-chain or branched dialkylamino group having 2–8 carbon atoms, the cyclohexylamino group, the anilino group, the piperidyl group or the morpholinyl group, (e) p is 3-n'-n" and A is a radical of the formula Xa

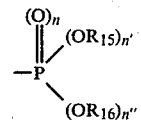

wherein n, n' and n" independently of one another denote 0 or 1, $R_{15}$ and $R_{16}$ independently of one another denote hydrogen, a straight-chain or branched alkyl group having 1–8 carbon atoms, or the phenyl group or $R_{15}$ and $R_{16}$ conjointly denote a 1,2-alkylene group having 2–3 carbon atoms, a 1,3-alkylene group having 3–5 carbon atoms, o-phenylene or a group of the formula

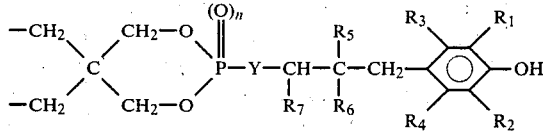

(f) p is 2-n' and A is a radical of the formula XI

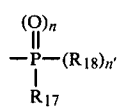 (XI)

wherein n and n' independently of one another denote 0 or 1, $R_{17}$ denotes a straight-chain or branched alkyl group having 1–6 carbon atoms, the benzyl group, a benzyl group substituted by 1 or 2 alkyl groups which each have 1–5 carbon atoms, and/or by a hydroxyl group, and $R_{18}$ denotes a straight-chain or branched alkoxy group having 1–8 carbon atoms, the phenoxy group or a straight-chain or branched alkyl group having 1–6 carbon atoms.

(3) Compounds of the formula I in which $R_1$ denotes alkyl having 1–4 carbon atoms, $R_2$ denotes alkyl having 3–4 carbon atoms, $R_3$ and $R_4$ denote hydrogen, $R_5$ denotes alkyl having 1–4 carbon atoms, $R_6$ denotes alkyl having 1–4 carbon atoms, or, conjointly with $R_5$, denotes alkylene having 4–5 carbon atoms, $R_7$ denotes hydrogen or alkyl having 1–8 carbon atoms, or, conjointly with $R_5$ or $R_6$, denotes tetramethylene, Y denotes —O— or —NH— and p denotes 1, 2, 3 or 4, and p and A have the following meaning:

(a) p is 1 to 4 and A is a radical of the formula II $R_8$—CO—           (II)

wherein, if p is equal to 1, $R_8$ denotes a straight-chain or branched alkyl group having 1–18 carbon atoms, an alkenyl group having 2–3 carbon atoms, the cyclohexyl group, an aralkyl group having 7–10 carbon atoms, an aralkyl group substituted by 1 or 2 alkyl groups which each have 1–4 carbon atoms, and/or by a hydroxyl group, a thiaalkyl group having 2–21 carbon atoms, the phenyl group, a phenyl group substituted by 1 or 2 alkyl groups which each have 1–4 carbon atoms, and/or by a hydroxyl group, a straight-chain or branched alkylamino group having 1–4 carbon atoms, a straight-chain or branched dialkylamino group having 2–8 carbon atoms, the anilino group, a straight-chain or branched alkoxy group having 1–18 carbon atoms, a cycloalkoxy group having 5–8 carbon atoms, the benzyloxy group, the phenoxy group or a phenoxy group which has 7–14 carbon atoms and which is substituted by 1 to 2 alkyl groups, or p is 2 and A is a group of the formula III

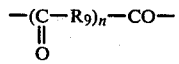 (III)

wherein n denotes 0 or 1, and $R_9$ denotes a direct bond, a straight-chain or branched alkylene group having 1–8 carbon atoms, a thiaalkylene group having 2–4 carbon atoms, an alkylthioalkylene group having 3–20 carbon atoms, a phenylene group, a straight-chain or branched alkylenediamino group having 2–6 carbon atoms, the diphenylmethane-4,4'-diamino group, or a straight-chain or branched alkylenedioxy group having 2–6 carbon atoms or p is 3 and A is a group of the formula IV

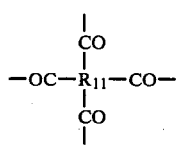 (IV)

wherein $R_{10}$ denotes an alkanetriyl group having 1–8 carbon atoms, or a phenyltriyl group, or p is 4 and A is a group of the formula VI

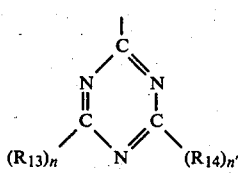 (VI)

wherein $R_{11}$ denotes an alkanetetrayl group having 2–8 carbon atoms, (c) p is 3-n-n' and A is a radical of the formula VIII

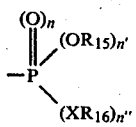 (VIII)

wherein n and n' independently of one another denote 0 or 1, and $R_{13}$ and $R_{14}$ independently of one another denote a straight-chain or branched alkoxy group having 1–12 carbon atoms, a straight-chain or branched alkylthio group having 1–12 carbon atoms, an alkoxycarbonylalkylthio group having 3–10 carbon atoms; a straight-chain or branched alkylamino group having 1–8 carbon atoms, a straight-chain or branched dialkylamino group having 2–8 carbon atoms, the piperidyl group or the morpholinyl group, (e) p is 3-n'-n'' and A is a radical of the formula Xa

 (Xa)

wherein n, n' and n'' independently of one another denote 0 or 1, $R_{15}$ and $R_{16}$ independently of one another denote hydrogen, a straight-chain or branched alkyl group having 1–8 carbon atoms, the phenyl group or $R_{15}$ and $R_{16}$ conjointly denote a 1,2-alkylene group having 2–3 carbon atoms, a 1,3-alkylene group having 3–5 carbon atoms, or o-phenylene or a group

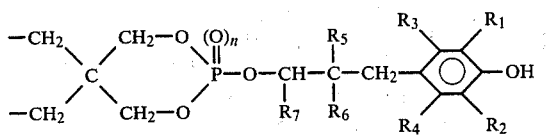

(f) p is 2 and A is a radical of the formula XI′

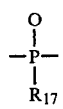
(XI′)

wherein $R_{17}$ denotes a straight-chain or branched alkyl group having 1-6 carbon atoms, or a benzyl group substituted by 1 or 2 alkyl groups which each have 1-5 carbon atoms, and/or by a hydroxyl group.

(4) Compounds of the formula I in which $R_1$ denotes alkyl having 1-4 carbon atoms, $R_2$ denotes tert.butyl, $R_3$ and $R_4$ denote hydrogen, $R_5$ and $R_6$ denote methyl and $R_7$ denotes hydrogen, Y denotes —O— or —NH— and p denotes 1, 2, 3 or 4, and p and A have the following meaning:

(a) p is 1 to 4 and A is a radical of the formula II $$R_8-CO-\qquad(II)$$

wherein, if p is equal to 1, $R_8$ denotes a straight-chain or branched alkyl group having 1-18 carbon atoms, the benzyl group, an aralkyl group substituted by 1 or 2 alkyl groups which each have 1-4 carbon atoms, and/or by a hydroxyl group, a thiaalkyl group having 2-21 carbon atoms, the phenyl group, a phenyl group substituted by 1 or 2 alkyl groups which each have 1-4 carbon atoms, and/or by a hydroxyl group, a straight-chain or branched alkylamino group having 1-4 carbon atoms, the anilino group, a straight-chain or branched alkoxy group having 1-18 carbon atoms, the benzyloxy group, the phenoxy group, a phenoxy group which has 7-14 carbon atoms and which is substituted by 1 to 2 alkyl groups, or a naphthoxy group, or p is 2 and A is a group of the formula III

(III)

wherein n denotes 0 or 1, and $R_9$ denotes a direct bond, a straight-chain or branched alkylene group having 1-8 carbon atoms, a thiaalkylene group having 2-4 carbon atoms, a phenylene group, a straight-chain or branched alkylenediamino group having 2-6 carbon atoms, the diphenylmethane-4,4′-diamino group, a straight-chain or branched alkylenedioxy group having 2-6 carbon atoms, or p is 3 and A is a group of the formula IV

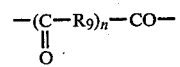
(IV)

wherein $R_{10}$ denotes a phenyltriyl group, or p is 4 and A is a group of the formula VI

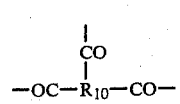
(VI)

wherein $R_{11}$ denotes an alkanetetrayl group having 2-8 carbon atoms, (e) p is 3-n′-n″ and A is a radical of the formula Xa

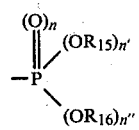
(Xa)

wherein n, n′ and n″ independently of one another denote 0 or 1, $R_{15}$ and $R_{16}$ independently of one another denote hydrogen, a straight-chain or branched alkyl group having 1-8 carbon atoms, or the phenyl group or $R_{15}$ and $R_{16}$ conjointly denote a 1,2-alkylene group having 2-3 carbon atoms, a 1,3-alkylene group having 3-5 carbon atoms, or o-phenylene or a group

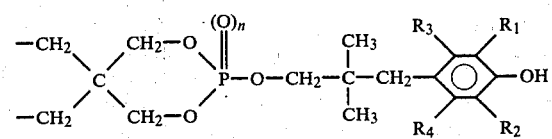

(5) Compounds of the formula I in which $R_1$ denotes alkyl having 1-4 carbon atoms, $R_2$ denotes tert.-butyl, $R_3$ and $R_4$ denote hydrogen, $R_5$ and $R_6$ denote methyl and $R_7$ denotes hydrogen, Y denotes —O— or —NH— and (a) p is 2 and A is a radical of the formula IIIa $$-CO-R_9-CO-\qquad(IIIa)$$

wherein $R_9$ denotes a straight-chain or branched alkylene group having 1-8 carbon atoms, or a thiaalkylene group having 2-4 carbon atoms, and (e) p is 3-n′-n″ and A is a radical of the formula Xa

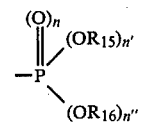
(Xa)

wherein n, n′ and n″ independently of one another denote 0 or 1, and $R_{15}$ and $R_{16}$ independently of one another denote a straight-chain or branched alkyl group having 1-8 carbon atoms or the phenyl group or $R_{15}$ and $R_{16}$ conjointly denote a group of the formula

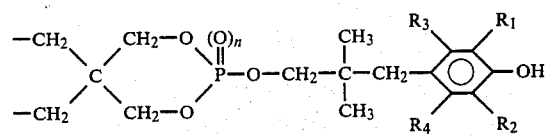

Examples of compounds of the formula I are: trimethylacetic acid 3-(3,5-ditert.butyl-4-hydroxyphenyl)-2,2-dimethylpropyl ester, 2-ethylcaproic acid 3-(3,5-ditert.butyl-4-hydroxyphenyl)-2,2-dimethylpropyl ester, 3-thiaheneicosanoic acid 3-(3,5-ditert.butyl-4-hydroxyphenyl)-2,2-dimethylpropyl ester, 2,2,4-trimethyladipic acid bis[3-(3,5-ditert.butyl-4-hydroxyphenyl)-2,2-dimethylpropyl ester], ethane-1,1,2,2-tetracarboxylic acid tetrakis-[3-(3,5-ditert.butyl-4-hydroxyphenyl)-2,2-dimethylpropyl ester], thiodisuccinic acid bis[3-(3,5-ditert.butyl-4-hydroxyphenyl)-2,2-dimethylpropyl ester], cyclohexane-1,4-dicarboxylic acid bis[3-(3,5-ditert.butyl-4-hydroxyphenyl)-2,2-dimethylpropyl ester], ethylthionothiolcarbonic acid 3-(3,5-ditert.butyl-4-hydroxyphenyl)-2,2-dimethylpropyl ester, thionocarbonic acid bis[3-(3,5-ditert.butyl-4-hydroxyphenyl)-2,2-dimethylpropyl ester], methylthionic acid 3(3,5-ditert.butyl-4-hydroxyphenyl)-2,2-dimethylpropyl ester, cyclohexanecarboxylic acid 3-(3,5-ditert.butyl-4-hydroxyphenyl)-2-ethyl-2-n-butylpropyl ester, thiodipropionic acid bis[3-(2,3-dimethyl-4-hydroxy-5-tert.butylphenyl)-2,2-dimethylpropyl ester], lauric acid 3-(3-methyl-4-hydroxy-5-tert.butylphenyl)-2,2-dimethylpropyl ester, stearic acid 3-(3-methyl-4-hydroxy-5-tert.butylphenyl)-2,2-dimethylpropyl ester, sebacic acid bis[3-(3-methyl-4-hydroxy-5-tert.butylphenyl)-2,2-dimethylpropyl ester], 4-octyloxybenzoic acid 3-(3-methyl-4-hydroxy-5-tert.butylphenyl)-2,2-dimethylpropyl ester, phenylacetic acid 3-(3-methyl-4-hydroxy-5-tert.butylphenyl)-2,2-dimethylpropyl ester, diphenylmethane-4,4'-dicarbamic acid bis[3-(3-methyl-4-hydroxy-5-tert.butylphenyl)-2,2-dimethylpropyl ester], dodecylthiocarbonic acid 3-(3-methyl-4-hydroxy-5-tert.butylphenyl)-2,2-dimethylpropyl ester, phosphorous acid tris[3-(3-methyl-4-hydroxy-5-tert.butylphenyl)-2,2-dimethylpropyl ester], pelargonic acid 3-(3,5-diisopropyl-4-hydroxyphenyl)-2,2-dimethylpropyl ester, succinic acid bis-3[3,5-bis(1-methylcyclohexyl)-4-hydroxyphenyl]-2,2-dimethylpropyl ester, fumaric acid bis[1-(3,5-ditert.butyl-4-hydroxybenzyl)-cyclohexylmethyl ester], palmitic acid 1-(3,5-ditert.butyl-4-hydroxybenzyl)-bicyclo [4,4,0]-decan-2-yl ester, N[3-(3,5-ditert.butyl-4-hydroxyphenyl)-2,2-dimethylpropyl]-4-acetoxybenzoic acid amide, N[3-(3,5-ditert.butyl-4-hydroxyphenyl)-2,2-dimethylpropyl]-3-(3,5-ditert.butyl-4-hydroxyphenyl)propionic acid amide.

The compounds of the formula I wherein A denotes a group derived from an organic or inorganic oxygen acid $A\text{-}(OH)_p$, are prepared, quite generally, by reacting an alcohol or amine of the formula XVIII

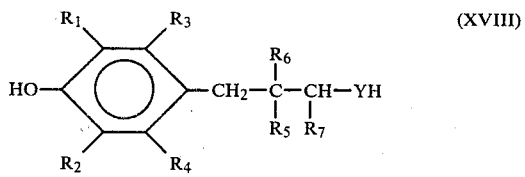

with a free oxygen acid of the formula XIX

$A\text{-}(OH)_p$            (XIX)

or, advantageously, with a reactive derivative of an oxygen acid.

Examples of alcohols of the formula XVIII are: 3-(3,5-ditert.butyl-4-hydroxyphenyl)-2,2-dimethyl-1-propanol, 3-(3-methyl-4-hydroxy-5-tert.butylphenyl)-2,2-dimethyl-1-propanol, 3-(3,5-diisopropyl-4-hydroxyphenyl)-2,2-dimethyl-1-propanol, 3-[3,5-bis(1-methylcyclohexyl)-4-hydroxyphenyl]-2,2-dimethyl-1-propanol, 3-(3,5-ditert.butyl-4-hydroxyphenyl)-2-ethyl-2-n-butyl-1-propanol, 1-(3,5-ditert.butyl-4-hydroxybenzyl)-1-hydroxymethyl-cyclohexane, 3-(2,3-dimethyl-4-hydroxy-5-tert.butylphenyl)-2,2-dimethyl-1-propanol, 2,2-bis(3,5-ditert.butyl-4-hydroxybenzyl)-ethanol, 1-(3,5-ditert.butyl-4-hydroxybenzyl)-bicyclo[4,4,0]-decan-2-ol, 3-(3,5-

Examples of compounds which are suitable as amines of the formula XVIII are: 3-(3,5-ditert.butyl-4-hydroxyphenyl)-2,2-dimethyl-1-propylamine and 2,2-bis(3,5-ditert.butyl-4-hydroxybenzyl)-ethylamine.

Examples of acids of the formula XIX are: p-basic carboxylic acids, p-basic thiocarboxylic acids, p-basic carbamic acids, 1-basic or 2-basic thiocarbamic acids, 1-basic or 2-basic carbonic acids, 1-basic or 2-basic thiocarbonic acids, 1-basic or 2-basic dithiocarbonic acids, mono-, di- or trihydroxytriazine, 2-hydroxybenzthiazole, 1-3-basic phosphorus oxyacids, 1-2-basic sulphur oxyacids, 1-3-basic boron oxyacids or p-basic silicon oxyacids, such as, for example, saturated aliphatic monocarboxylic acids, such as formic acid, acetic acid, propionic acid, butyric acid, valeric acid, trimethylacetic acid, caproic acid, oenanthic acid, caprylic acid, pelargonic acid, capric acid, 2-ethylcaproic acid, lauric acid, myristic acid, palmitic acid, margaric acid, stearic acid, arachidic acid, 12-hydroxystearic acid, monochloroacetic acid, dichloroacetic acid, β-monochloropropionic acid, 3-thiapentanoic acid, 3-thiaheneicosanoic acid, 4-thiaoctanoic acid and 4-thiahexadecanoic acid.

Saturated aliphatic dicarboxylic acids and monoesters and monoamides thereof, such as oxalic acid, malonic acid, succinic acid, glutaric acid, adipic acid, pimelic acid, suberic acid, azelaic acid, 2,2,4-trimethyladipic acid, sebacic acid, nonanedicarboxylic acid, decanedicarboxylic acid, undecanedicarboxylic acid, malic acid, oxalic acid monoethyl ester, adipic acid monododecyl ester, oxalic acid mono(butylamide), oxalic acid mono(dialkylamide), and sebacic acid mono(octylamide).

Saturated aliphatic tricarboxylic acids, such as citric acid.

Saturated aliphatic tetracarboxylic acids, such as ethane-1,1,2,2-tetracarboxylic acid.

Unsaturated aliphatic carboxylic acids, such as fumaric acid, crotonic acid, oleic acid, acetylenedicarboxylic acid, thiodipropionic acid or thiodisuccinic acid.

Saturated cycloaliphatic carboxylic acids, such as cyclopentanecarboxylic acid, cyclohexanecarboxylic acid, cyclooctanecarboxylic acid, cyclohexane-1,4-dicarboxylic acid or cyclopropane-1,2,3-tricarboxylic acid.

Unsaturated cycloaliphatic carboxylic acids, such as 3-cyclohexene-1-carboxylic acid.

Unsubstituted and substituted benzoic acids, such as benzoic acid, salicylic acid, 2,4-dichlorobenzoic acid, 2,4-dimethylbenzoic acid, 4-tert.butylbenzoic acid, 4-octyloxybenzoic acid, 4-acetoxybenzoic acid, terephthalic acid monoethyl ester, acetylsalicylic acid, 2-benzoylbenzoic acid, thiosalicylic acid, terephthalic acid or pyromellitic acid.

Unsubstituted and substituted aralkylcarboxylic acids, such as phenylacetic acid, diphenylacetic acid, o-hydroxy-phenylacetic acid, mandelic acid, 3-(3,5- ditert.butyl-4-hydroxyphenyl)propionic acid or cinnamic acid.

Heterocyclic carboxylic acids, such as 2-furanecarboxylic acid, 2-thiophenecarboxylic acid or nicotinic acid.

Carbonic acid and monoesters thereof, such as carbonic acid, carbonic acid monododecyl ester, 1,6-hexanediol-O,O-dicarboxylic acid, carbonic acid monophenyl ester, hydroquinone-O-O-dicarboxylic acid esters, carbonic acid monobenzyl ester or carbonic acid mono-β-naphtyl ester.

Carbamic acids, such as n-butylcarbamic acid, di-(n-octyl)carbamic acid, cyclohexylcarbamic acid, phenylcarbamic acid, diphenylcarbamic acid, 4-chlorophenylcarbamic acid, 2-methylphenylcarbamic acid, hexamethylenedicarbamic acid, N,N'-dimethylhexamethylenedicarbamic acid or diphenylmethane-4,4'-dicarbamic acid.

Thionic acids or thiocarbonic acid and monoesters thereof, such as dodecylthiocarbonic acid, phenylthiocarbonic acid, methylthionocarbonic acid, ethylthionothiolcarbonic acid, thionocarbonic acid, methylthionic acid or phenylthionic acid.

Cyanuric acid or mono- and di-esters and mono- and di-amides of cyanuric acid and of the thiocyanuric acids, such as cyanuric acid mono-n-butyl ester, cyanuric acid diphenyl ester, cyanuric acid bis(diethylamide), cyanuric acid dimorpholide, cyanuric acid monopiperidide; thiocyanuric acid S-monomethyl ester or dithiocyanuric acid S,S-didecyl ester.

Phosphoric acid, thiophosphoric acid and monoesters and diesters thereof, such as phosphoric acid dimethyl ester, monothiophosphoric acid O,O-dioctyl ester, phosphoric acid phenyl ester, phosphoric acid diphenyl ester, phosphoric acid phenylene ester or phosphoric acid 1,2-propylene ester.

Phosphorous acid and monoesters and diesters thereof, such as phosphorous acid, phosphorous acid diphenyl ester, phosphorous acid ethylene ester or phosphorous acid octadecyl ester.

Phosphonic acid and monoesters thereof, such as phenylphosphonic acid, 3,5-ditert.butyl-4-hydroxybenzylphosphonic acid, benzylphosphonic acid monoethyl ester or methylphosphonic acid monomethyl ester.

Phosphinic acids, such as dibutylphosphinic acid.

Phosphonous acids and monoesters thereof, such as phenylphosphonous acid monopentyl ester or benzylphosphonous acid.

Phosphinous acids, such as dibenzylphosphinous acid.

Sulphonic acids, such as p-toluenesulphonic acid, α-naphthalenesulphonic acid or 2,4-benzenedisulphonic acid.

The reaction of the compounds of the formula XVIII with the compounds of the formula XIX is carried out by known methods for esterifying alcoholic hydroxyl groups; it can be carried out with or without the use of a solvent; a catalyst can be used additionally, as can a hydrogen halide acceptor. The choice of a solvent or of a catalyst and the choice of the reaction temperature depend on the particular reaction components used; the working up also depends on the reaction components. These methods of esterifying alcoholic hydroxy compounds with carboxylic acids and derivatives thereof are, in general, adequately known, as are the methods of isolating the esterified reaction products.

A suitable reactive derivative of the oxyacid is, in particular, the acid halide thereof XIXa $$A\text{-}(Z)_p \qquad (XIXa)$$

wherein Z denotes chlorine or bromine, or the ester thereof XIXb $$A\text{-}(OR_{22})_p \qquad (XIXb)$$

wherein $R_{22}$ denotes a lower alkyl group, preferably methyl or ethyl, or the phenyl group, or the anhydride thereof XIXc $$A\text{-}O\text{-}A \qquad (XIXc)$$

or, if A denotes a N-monosubstituted carbamic acid, the isocyanate thereof.

Depending on the structure of the esters, urethanes, amides or ureas formed, the latter can be accessible to further reactions in which further compounds which fall under the claim are formed. Such a sequence of reactions is occasionally advantageous, but the esters formed can also be directly prepared from alcohol or amine and the corresponding reactive acid derivative by one of the abovementioned general methods.

Among the secondary reactions, the following should be mentioned particularly:

(a) Oxidation of an ester of the phosphorous acid of the formula XX

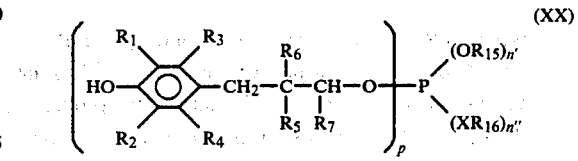

wherein $R_1$ to $R_7$ have the meaning defined in formula I and $R_{15}$, $R_{16}$, p, n' and n'' have the meaning defined in formula X, by means of hydrogen peroxide, cumene hydroperoxide or atmospheric oxygen to give the corresponding ester of the phosphoric acid of the formula XXI

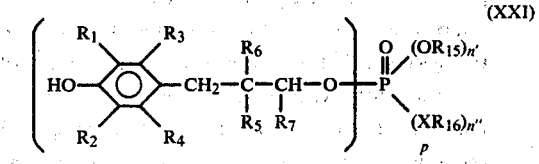

(b) Oxidation of an ester of a phosphonous or phosphinous acid of the formula XXII

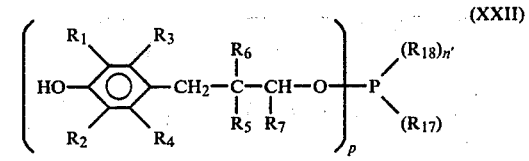

wherein $R_1$ to $R_7$ have the meaning defined in formula I and $R_{17}$, $R_{18}$, p and n' have the meaning defined in formula XI, by means of hydrogen peroxide, cumene hydroperoxide or atmospheric oxygen to give the corresponding ester of a phosphonic acid or phosphinic acid of the formula XXIII

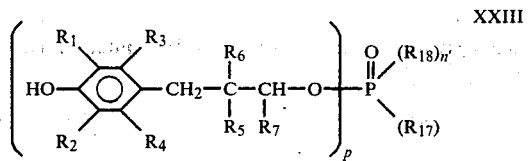

XXIII (c) Alkylation of a diester of the phosphorous acid or of a monoester of a phosphonous acid of the formula XXIV

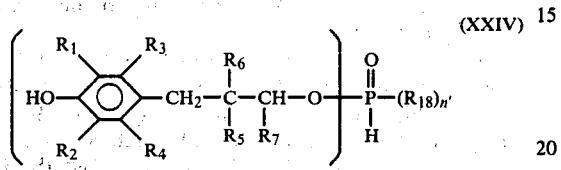

(XXIV)

wherein $R_1$ to $R_7$ have the meaning defined in formula I and $R_{18}$, p and n' have the meaning defined in formula XI, by means of an alkylating compound of the formula XXV $R_{17}$-Z'    (XXV)

wherein $R_{17}$ has the meaning defined in formula XI and Z' denotes chlorine or bromine or, if $R_{17}$ has the meaning of an optionally alkyl-substituted hydroxybenzyl group, also a group of the formulae

to give an ester of a phosphonic acid or of a phosphinic acid of the formula XXIII.

(d) Substitution of a reactive group in the group A of the formula I, for example the substitution of a chlorine atom with the aid of an alcohol, mercaptan or dialkyl phosphite to give the corresponding compound substituted by alkoxy, alkyl-mercapto or dialkoxyphosphoryl, for example

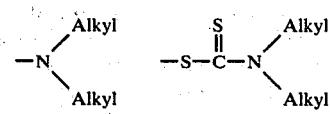

wherein $R_{23}$ denotes an alkyl group, or

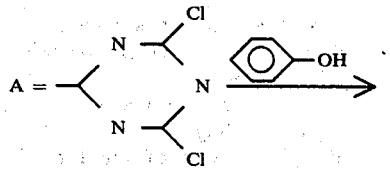

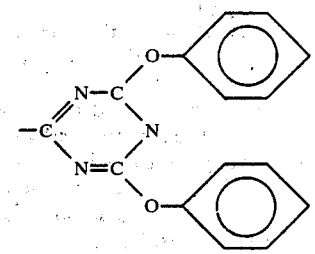

(e) Addition reaction with a reactive grouping in the group A of the formula I, for example the addition reaction of a mercaptan with a double bond:

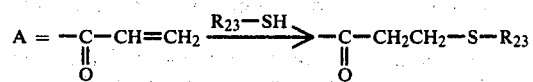

wherein $R_{23}$ denotes an alkyl group.

(f) Reaction of a chlorocarbonic acid ester of the formula XXVI

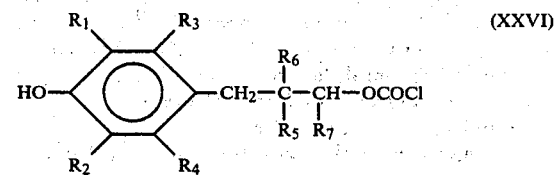

(XXVI)

with an alcohol, mercaptan or amine, for example

XXVI + $C_6H_5NH_2$ ⟶

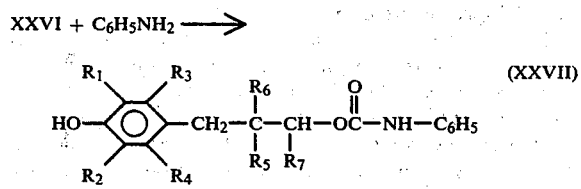

(XXVII)

(g) Reaction of an isocyanate of the formula XXVIII

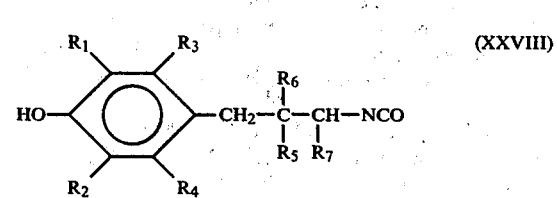

(XXVIII)

with an alcohol, mercaptan or amine, for example

XXVIII + $C_6H_5NH_2$ ⟶    (XXIX)

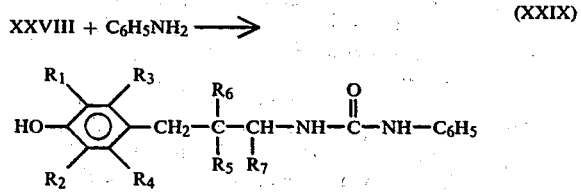

The alcohols of the formula XVIII wherein —Y— denotes —O—, which are required as starting compounds for the preparation of the esters of the formula I, can be prepared by hydrogenating the corresponding aldehydes or ketones of the formula XXX

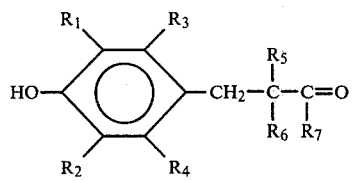 (XXX)

in which $R_1$ to $R_7$ have the meaning indicated under formula I. The hydrogenation is carried out under pressure, by known processes, in the presence of a noble metal catalyst, such as Raney nickel, in a solvent, for example in an alcohol, such as methanol, ethanol or propanol.

The amines of the formula XVIII wherein —Y— denotes —NH—, which are required for the preparation of the amides of the formula I, can be prepared by hydrogenating the aldehydes or ketones of the formula XXX in the presence of ammonia. The hydrogenation is carried out under pressure, by known processes, in the presence of a noble metal catalyst, for example Raney nickel, in a solvent.

The aldehydes or ketones of the formula XXX which are required as starting compounds for the preparation of the alcohols of the formula XVIII, can be prepared by reacting a compound of the formula XXXI

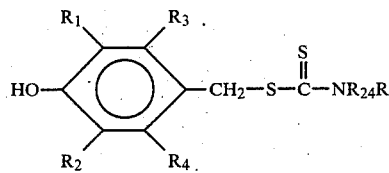 (XXXI)

wherein $R_1$ to $R_4$ have the meaning defined in formula I and $R_{24}$ and $R_{25}$ independently of one another denote alkyl, or, with the inclusion of the nitrogen atom, conjointly denote a saturated, heterocyclic 5-membered or 6-membered ring, with a compound of the formula XXXII

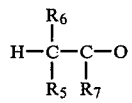 (XXXII)

wherein $R_5$, $R_6$ and $R_7$ have the same meaning as in formula I.

The process is carried out, for example, in a solvent. Suitable solvents are alcohols, such as methanol, ethanol, iso-propanol, sec.butanol, tert.butanol or amyl alcohol, aliphatic ethers, such as dibutyl ether, tetrahydrofurane or dioxane, hydrocarbons, such as hexane, heptane, octane, ligroin, decalin, cyclohexane, benzene, toluene or xylene, or aprotic polar solvents, such as dimethylformamide, dimethylacetamide or dimethylsulphoxide.

Examples of suitable bases in the process are alkali metal hydroxides, such as sodium hydroxide or potassium hydroxide, alcoholates, such as sodium methylate, sodium ethylate, magnesium ethylate, potassium isopropylate or potassium tert.butylate, or hydrides, such as lithium hydride, sodium hydride or potassium hydride.

The temperatures at which the process is carried out are, for example, between $-10°$ and $+120°$ C.

The process is preferably carried out under an atmosphere of nitrogen or noble gas. The base can be initially introduced into the solvent and the starting compounds can be added jointly or separately, optionally in a dissolved form.

The compounds of the formula I are used as stabilisers for organic substrates. As such it is possible to use, for example:

1. Polymers which are derived from hydrocarbons with single or double unsaturation, such as polyolefines, such as, for example, polyethylene, which can optionally be cross-linked, polypropylene, polyisobutylene, polymethylbutene-1, polymethylpentene-1, polyisoprene, polybutadiene and polyisobutylene.

2. Mixtures of the homopolymers mentioned under 1, such as, for example, mixtures of polypropylene and polyethylene, polypropylene and polybutene-1, polypropylene and polyisobutylene.

3. Copolymers of the monomers on which the homopolymers mentioned under 1 are based, such as ethylene-propylene copolymers, propylene-butene copolymers, propylene-isobutylene copolymers, ethylene-butene-1 copolymers and terpolymers of ethylene and propylene with a diene, such as, for example, hexadiene, dicyclopentadiene or ethylidene norbornene.

4. Polystyrene.

5. Copolymers of styrene and of $\alpha$-methylstyrene, such as styrene-butadiene copolymers, styrene-acrylonitrile copolymers, styrene-acrylonitrile-methylmethacrylate copolymers, styrene-acrylonitrile-acrylic ester copolymers, styrene-acrylonitrile copolymers modified with acrylic ester polymers so as to have improved impact strength, and styrene polymers modified with EPDM so as to have improved impact strength.

6. Graft copolymers of styrene, such as, for example, the graft polymer of styrene on polybutadiene, the graft polymer of styrene with acrylonitrile on polybutadiene and mixtures thereof with the copolymers mentioned under 5, commonly designated as acrylonitrile-butadiene-styrene or ABS plastics.

7. Vinyl polymers containing halogen, such as polyvinyl chloride, polyvinylidene chloride, polyvinyl fluoride, polychloroprene, chlorinated rubbers, vinyl chloride-vinylidene chloride copolymers, vinyl chloride-vinyl acetate copolymers and vinylidene chloride-vinyl acetate copolymers.

8. Polymers which are derived from $\alpha,\beta$-unsaturated acids and their derivatives, polyacrylates and polymethacrylates, polyacrylamides and polyacrylonitrile.

9. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

10. Homopolymers and copolymers which are derived from epoxides, such as polyethylene oxide or the polymers which are derived from bis-glycidyl ethers.

11. Polyacetals, such as polyoxymethylene, as well as those polyoxymethylenes which contain ethylene oxide as the comonomer.

12. Polyalkylene oxides, such as polyoxyethylene, polypropylene oxide or polyisobutylene oxide.

13. Polyphenylene oxides.

14. Polyurethanes and polyureas.

15. Polycarbonates.
16. Polysulphones.
17. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.
18. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.
19. Crosslinked polymers which are derived from aldehydes on the one hand and phenols, ureas and melamines on the other, such as phenol-formaldehyde, urea-formaldehyde and melamine-formaldehyde resins.
20. Alkyd resins, such as glycerol-phthalic acid resins and their mixtures with melamine-formaldehyde resins.
21. Unsaturated polyester resins which are derived from copolyesters of saturated and unsaturated dicarboxylic acids with polyhydric alcohols, with vinyl compounds as cross-linking agents, and also their halogen-containing modifications of low inflammability.
22. Natural polymers, such as cellulose, rubber, proteins and their polymer-homologously chemically modified derivatives, such as cellulose acetates, cellulose propionates and cellulose butyrates, or the cellulose ethers, such as methylcellulose.
23. Natural and synthetic organic substances which are pure monomeric compounds or mixtures of such, for example mineral oils, animal and vegetable fats, oils and waxes, or oils, waxes and fats based on synthetic esters and mixtures of synthetic esters with mineral oils in any desired weight ratios.

The compounds of the formula I are incorporated in the substrates in a concentration of 0.005 to 5% by weight, relative to the material to be stabilised.

Preferably, 0.01 to 1.0, particularly preferably 0.02 to 0.5, % by weight of the compounds, relative to the material to be stabilized, are incorporated into the latter. The incorporation can be carried out, for example, by mixing in at least one of the compounds of the formula I and optionally further additives by the methods customary in the art, before or during shaping, or by applying the compounds, dissolved or dispersed, to the polymer, where appropriate with subsequent evaporation of the solvent.
pounds are added before the crosslinking.

The compounds of the formula I can also be added before or during the polymerisation, it being possible, by a potential incorporation into the polymer chain, to obtain stabilised substrates in which the stabilisers are not volatile or extractable.

The following may be mentioned as examples of further additives with which the stabilisers can be conjointly employed:
1. Antioxidants
1.1 Simple 2,6-dialkylphenols, such as, for example, 2,6-ditert.-butyl-4-methylphenol, 2-tert.-butyl-4,6-dimethylphenol, 2,6-di-tert.-butyl-4-methoxymethylphenol and 2,6-dioctadecyl-4-methylphenol.
1.2 Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl) phosphite 3,5-di-tert.-butyl-4-hydroxyphenyl stearate and bis-(3,5-di-tert.-butyl-4-hydroxyphenyl) adipate.
1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.
1.4 Alkylidene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-di-tert.butyl-phenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercaptobutane, 1,1,5,5-tetra-(5-tert.butyl-4-hydroxy-2-methylphenyl)-pentane and ethylene glycol bis-[3,3-bis-(3'-tert.butyl-4'-hydroxyphenyl)-butyrate].
1.5 O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithiol-terephthalate.
1.6 Hydroxybenzylated malonic esters, such as, for example, 2,2-bis-(3,5-di-tert.butyl-4-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid di-dodecylmercapto-ethylester and 2,2-bis-(3,5-di-tert.butyl-4-hydroxybenzyl)-malonic acid di-[4-(1,1,3,3-tetramethylbutyl)-phenyl]-ester.
1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.
1.8 s-Triazine compounds, such as, for example 2,4-bis-octylmercapto-6-(3,5-di-tert.butyl-4-hydroxy-anilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.
1.9 Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.
1.10 Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11 Esters of β-(5-tert.butyl-4-hydroxy-3-methylphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.12 Esters of 3,5-di-tert.butyl-4-hydroxyphenylacetic acid with monohydric or polyhydric alcohols, such as, for example, methanol, ethanol, octadecanol, 1,6-hexanediol, 1.9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.13 Acylaminophenols, such as, for example, N-(3,5-di-tert.butyl-4-hydroxyphenyl)-stearic acid amide and N,N'-di-(3,5-di-tert.butyl-4-hydroxyphenyl)-thiobis-acetamide.

1.14 Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15 Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline. Octylated diphenylamine, nonylated diphenylamine, N-phenyl-N-cyclohexyl-p-phenylenediamine, N-phenyl-N'-isopropyl-p-phenylenediamine, N,N'-di-sec.octyl-p-phenylenediamine, N-phenyl-N-sec.octyl-p-phenylenediamine, N,N'-di-(1,4-dimethylpentyl)-p-phenylenediamine, N,N'-dimethyl-N,N'-di-(sec.octyl)-p-phenylenediamine, 2,6-dimethyl-4-methoxyaniline, 4-ethoxy-N-sec.butylaniline, the condensation product of diphenylamine and acetone, and phenothiazine.

2. UV absorbers and light stabilisers 2.1 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.-butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.amyl derivative.

2.2 2,4-Bis-(2'-hydroxyphenyl)-6-alkyl-s-triazines, such as, for example, the 6-ethyl-, 6-heptadecyl or 6-undecyl derivative.

2.3 2-Hydroxy-benzophenones, such as, for example, the 4-hydroxy-, 4-methoxy-, 4-octoxy-, 4-decyloxy-, 4-dodecyloxy-, 4-benzyloxy, 4,2',4'-trihydroxy- or 2'-hydroxy-4,4'-dimethoxy-derivative.

2.4 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5 Esters of optionally substituted benzoic acids such as, for example, phenyl salicylate, octylphenyl salicylate, dibenzoylresorcinol, bis-(4-tert.-butylbenzoyl)-resorcinol, benzoylresorcinol and 3,5-di-tert.butyl-4-hydroxybenzoic acid 2,4-di-tert.butyl-phenyl ester, octadecyl ester or 2-methyl-4,6-di-tert.butylphenyl ester.

2.6 Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methyl-indoline.

2.7 Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenylundecylketonoxime, nickel 3,5-di-tert.butyl-4-hydroxybenzoate, nickel isopropylxanthate and Ni complexes of 1-phenyl-4-lauroyl-5-hydroxypyrazole, optionally with additional ligands.

2.8 Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate, and 3-n-octyl-7,7,9,9-tetramethyl-1,3,8-triaza-spiro[4,5]decane-2,4-dione.

2.9 Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

2.10 N-Cyclohexyl-thiophosphoric acid O,O-di-(4-tert.butyl-phenyl) ester.

2.11 Co dicyclohexyl-dithiophosphinate.

3. Metal deactivators, such as, for example, oxanilide, isophthalic acid dihydrazide, sebacic acid bis-phenylhydrazide, bis-benzylidene-oxalic acid dihydrazide, N,N'-diacetyl-adipic acid dihydrazide, N,N'-bis-salicyloyl-oxalic acid dihydrazide, N,N'-bis-salicyloyl-hydrazine, N,N'-bis-(3,5-di-tert.butyl-4-hydroxyphenyl-propionyl)-hydrazine, N-salicylal-N'-salicyloyl-hydrazine and 3-salicyloylamino-1,2,4-triazole.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxa-3,9-diphosphaspiro[5,5]undecane, tri-(4-hydroxy-3,5-di-tert.butylphenyl)-phosphite and 3,9- di-octadecyloxy-2,4,8,10-tetraoxa-3,9-diphospaspiro[5,5]undecane.
5. Compounds which destroy peroxides, such as, for example, esters of β-thiodipropionic acid, for example the lauryl, stearyl, myristyl or tridecyl esters, mercapto-benzimidazole and the zinc salt of 2-mercapto-benzimidazole.
6. Polyamide stabilisers, such as, for example, copper salts in combination with iodides and/or phosphorus compounds and salts of divalent manganese.
7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate and antimony pyrocatecholate or tin pyrocatecholate.
8. PVC stabilisers, such as, for example, organic tin compounds, organic lead compounds and barium-cadmium salts of fatty acids.
9. Nucleating agents, such as for example 4-tert.butyl-benzoic acid, adipic acid and diphenylacetic acid.
10. Urea derivatives, such as, for example, N-cyclohexyl-N'-1-naphthylurea, N-phenyl-N,N'-dicyclohexylurea, N-phenyl-N'-2-naphthylurea, N-phenylthiourea and N,N'-dibutylthiourea.
11. Other additives, such as, for example, plasticisers, lubricants, emulsifiers, fillers, carbon black, asbestos, kaolin, talc, glass fibers, pigments, optical brighteners, flameproofing agents and antistatic agents.

The preparation and use of the compounds according to the invention are described in greater detail in the examples which follow. In these, parts denote parts by weight and % denotes percentages by weight.

EXAMPLE 1a

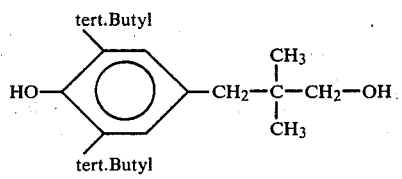

145 g (0.5 mol) of 3-(3,5-di-tert.butyl-4-hydroxyphenyl)-2,2-dimethylpropionaldehyde are dissolved in 1,500 ml of absolute ethanol, 15 g of Raney nickel are added and hydrogenation is carried out at room temperature and an initial pressure of 50 bars in a shaking autoclave for 3½ hours. Hydrogenation is then continued for a further 15 hours at 50° C. After cooling, the excess hydrogen is discharged and the catalyst is filtered off from the reaction mixture. The filtrate is concentrated completely under reduced pressure on a rotary evaporator. After recrystallisation from petroleum ether, the 3-(3,5-di-tert.butyl-4-hydroxyphenyl)-2,2-dimethylpropyl alcohol melts at 86° C.

EXAMPLE 1b

If, in Example 1a, the 3-(3,5-di-tert.butyl-4-hydroxyphenyl)-2,2-dimethylpropionaldehyde is replaced by an equivalent quantity of a 3-(3,5-dialkyl-4-hydroxyphenyl)-2,2-dimethylpropionaldehyde of the table which follows, the 3-(3,5-dialkyl-4-hydroxyphenyl)-2,2-dimethylpropyl alcohols having the melting points quoted are obtained.

| Aldehyde | Melting point of the alcohol |
|---|---|
| tert. Butyl | 95° C. |
| iso-Propyl | 100° C. |
| iso-Propyl / CH₃ | 132° C. |

EXAMPLE 1c 29 g (0.1 mol) of 3-(3,5-di-tert.butyl-4-hydroxyphenyl)-2,2-dimethylpropionaldehyde and 11.4 g (0.13 mol) of a 35% strength formaldehyde solution are dissolved in 50 ml of ethanol at 60° C. A solution of 22.4 g (0.4 mol) of potassium hydroxide in 17 ml of water is added to this dropwise over the course of 5 minutes. The reaction is exothermic and the temperature rises to approx. 70° C. The mixture is then stirred for a further 40 minutes at 70° C., and is then heated to the point of reflux and is allowed to boil for 20 minutes while stirring. The red-violet reaction mixture is cooled, neutralised with glacial acetic acid, taken up in toluene and washed twice with water. The toluene phase is concentrated completely under reduced pressure on a rotary evaporator. The oil which remains crystallises on standing. This gives 3-(3,5-di-tert.butyl-4-hydroxyphenyl)-2,2-dimethylpropyl alcohol of melting point 86° C.

EXAMPLE 1d

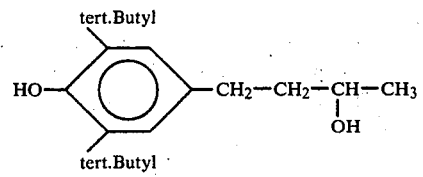

If, in Example 1, the 3-(3,5-di-tert.butyl-4-hydroxyphenyl)-2,2-dimethylprepionaldehyde is replaced by an equivalent quantity of methyl-(3,5-di-tert.butyl-4-hydroxyphenylethyl)-ketone, an otherwise identical procedure gives 4-(3,5-di-tert.butyl-4-hydroxyphenyl)-2-butanol of melting point 70° C.

EXAMPLES 2-20

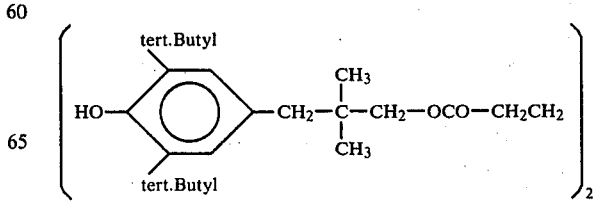

29.2 g (0.1 mol) of 3-(3,5-di-tert.butyl-4-hydroxyphenyl)-2,2-dimethyl-propanol are dissolved in 100 ml of pyridine. 9.1 g (0.05 mol) of adipic acid dichloride are added dropwise to the solution at room temperature over the course of 30 minutes. After the strongly exothermic reaction has subsided, the mixture is heated to 80° C. for a further 2 hours. It is poured into 500 ml of ice water and the resulting emulsion is acidified, whereupon the product crystallises. After being filtered off and dried, it is recrystallized from ligroin. This gives adipic acid di-3-(3,5-di-tert.butyl-4-hydroxyphenyl)-2,2-dimethylpropyl ester having a melting point of 133° C.

If, in this example, the adipic acid dichloride is replaced by an acid chloride of Table I which follows, using the quoted quantity which is equivalent to the 3-(3,5-di-tert.butyl-4-hydroxyphenyl)-2,2-dimethylpropanol employed, an otherwise identical procedure gives the 3-(3,5-di-tert. butyl-4-hydroxyphenyl)-2,2-dimethylpropyl ester having the melting points indicated. In the case of Example 11, the chlorocarbonic acid monoester is obtained.

TABLE I

| Example No. | Acid chloride | Equi-molecular quantity | Melting point of the reaction product |
|---|---|---|---|
| 3 | C₁₇H₃₅—COCl | 1 | 43° C. |
| 4 | benzene-1,3,5-tricarbonyl trichloride (COCl, COCl, COCl on benzene) | ⅓ | 180° C. |
| 5 | C₂H₅O—COCOCl | 1 | 77° C. |
| 6 | furan-2-carbonyl chloride (O-ring with COCl) | 1 | 121° C. |
| 7 | C₁₈H₃₇—OCOCl | 1 | 60° C. |
| 8 | CH₃—C(CH₃)₂—CH₂—C(CH₃)₂—C₆H₄—OCOCl | 1 | 130° C. |
| 9 | ClCOO—(CH₂)₆OCOCl | ½ | 132° C. |
| 10 | CH₃—C₆H₄—O—C(=S)—Cl | 1 | 74° C. |
| 11 | ClCOCl | 1 | 69° C. |
| 12 | ClSOCl | ½ | 115° C. |
| 13 | 3,5-di-tert.Butyl-4-hydroxyphenyl-COCl | 1 | 153° C. |
| 14 | CH₃—C₆H₄—SO₂Cl | 1 | 106° C. |
| 15 | (C₂H₅O)₂P(=O)Cl | 1 | Oil |
| 16 | PCl₃ | ⅓ | 127° C. |
| 17 | C₆H₅—O—PCl₂ | ½ | Oilˣ |
| 18 | SiCl₄ | ¼ | 134° C. |
| 19 | (CH₃)₃SiCl | 1 | 65° C. |
| 20 | (CH₃)₂SiCl₂ | ½ | 87° C. |

ˣAnalysis Calculated C 74.8 H 9.55 P 4.39
Found C 74.98 H 10.10 P 4.21

EXAMPLES 21–30

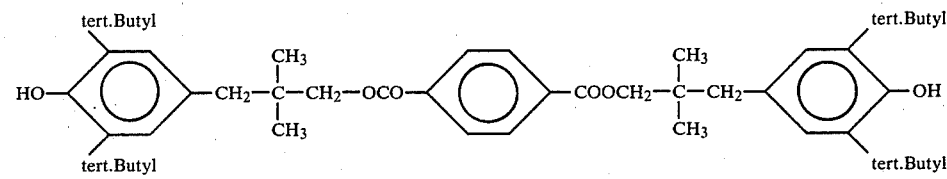

11.7 g (0.04 mol) of 3-(3,5-di-tert.butyl-4-hydroxyphenyl)-2,2-dimethylpropyl alcohol and 3.8 g (0.02 mol) of terephthalic acid dimethyl ester are melted at 140° C., a pinch of lithium amide is added and the mixture is evacuated to a pressure of 15 mm Hg and the temperature is kept at 140° C. for 30 minutes while stirring.

After cooling and releasing the vacuum with nitrogen, the whole melt is dissolved in hot dioxane. Terephthalic acid di-[3-(3,5-di-tert.-butyl-4-hydroxyphenyl)-2,2-dimethylpropyl] ester crystallises out on cooling and melts at 229° C.

If, in this example, the terephthalic acid dimethyl ester is replaced by one of the esters of Table II which follows, using a quantity equivalent to the 3-(3,5-di-tert.butyl-4-hydroxyphenyl)-2,2-dimethylpropanol employed, an analogous procedure gives the 3-(3,5-ditert.butyl-4-hydroxyphenyl)-2,2-dimethylpropyl esters with the melting points quoted.

TABLE II

| Example No. | Ester | Melting point of the reaction product |
|---|---|---|
| 22 | $CH_3OCO-CH_2-COOCH_3$ | 96° C. |
| 23 | [3,5-di-tert-butyl-4-hydroxyphenyl-CH$_2$-C(CH$_3$)$_2$-COOCH$_3$] | 166° C. |
| 24 | $CH_2=CH-COOCH_3$ | 79° C. |
| 25 | [N-COCOOC$_2$H$_5$ piperazine-N-COCOOC$_2$H$_5$] | 158° C. |
| 26 | $(C_2H_5O)_2P(O)H$ | 142° C. |
| 27 | $H_{37}C_{18}-S-CH_2CH_2-COOC_2H_5$ | 52° C. |
| 28 | $H_{17}C_8-S-CH_2-COOC_2H_5$ | boiling point 205° C./0.15 mm |
| 29 | $(H_5C_2OCOCH_2CH_2-S-CH_2-)_2$ | 165° C. |

EXAMPLE 31

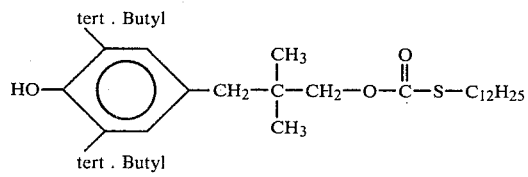

2.02 g (0.01 mol) of dodecylmercaptan and 1 g (0.0125 mol) of pyridine are together dissolved in 20 ml of dimethylacetamide. A solution of 3.5 g (0.01 mol) of chlorocarbonic acid 3-(3,5-di-tert.butyl-4-hydroxyphenyl)-2,2-dimethylpropyl ester (the product of Example 11) in 20 ml of dimethylacetamide is added dropwise at room temperature. The solution is kept for one hour at 80° C. and is then cooled and 150 ml of water are added. The product is extracted with ether and, after evaporating the solution, is crystallised from acetonitrile. This gives dodecylthiolcarbonic acid 3-(3,5-di-tert.butyl-4-hydroxyphenyl)-2,2-dimethylpropyl ester of melting point 45° C.

EXAMPLES 32–34

If, in Example 31, the dodecylmercaptan is replaced by an equivalent quantity of one of the compounds of Table III which follows, an anlogous procedure gives the 3-(3,5-di-tert.butyl-4-hydroxyphenyl)-2,2-dimethylpropyl esters having the melting points quoted.

TABLE III

| Example No. | Reagent | Melting point of the reaction product |
|---|---|---|
| 32 | [3,5-di-tert-butyl-4-hydroxyphenyl-CH$_2$-C(CH$_3$)$_2$-CH$_2$OH] | 200° C. |
| 33 | $C_2H-NH-C_2H_5$ | 130° C. |
| 34 | $C_8H_{17}-NH-C_8H_{17}$ | Oil |

EXAMPLES 35–38

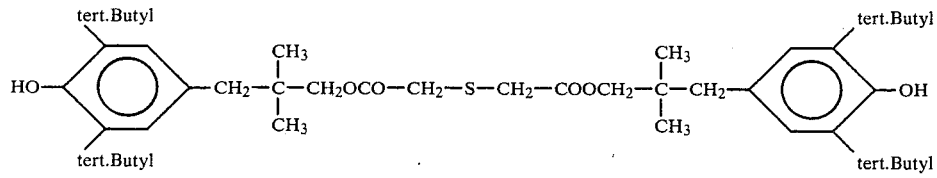

11.7 g (0.04 mol) of 3-(3,5-di-tert.butyl-4-hydroxyphenyl)-2,2-dimethylpropyl alcohol, 3 g (0.02 mol) of thiodiglycollic acid and 0.5 g of p-toluenesulphonic acid in 100 ml of toluene are heated to the point of reflux for 2 hours under a water separator. The reaction solution is then cooled and washed twice with water. The toluene phase is concentrated completely under reduced pressure and the residue is recrystallised from acetonitrile. The thiodiglycollic acid di-[3-(3,5-di-tert.butyl-4-hydroxyphenyl)-2,2-dimethylpropyl] ester thus obtained melts at 116° C.

If, in this example, the thiodiglycollic acid is replaced by one of the acids of Table IV which follows, using a quantity equivalent to the 3-(3,5-di-tert.butyl-4-hydroxyphenyl)-2,2-dimethylpropyl alcohol employed, an analogous procedure gives the 3-(3,5-di-tert.-butyl-4-hydroxyphenyl)-2,2-dimethylpropyl esters having the melting points quoted.

TABLE IV

| Example No. | Acid | Melting point of the reaction product |
|---|---|---|
| 36 | $HOOC-CH_2-CH_2-S-CH_2-CH_2COOH$ | 118° C. |

TABLE IV-continued

| Example No. | Acid | Melting point of the reaction product |
|---|---|---|
| 37 | Cl—CH$_2$—COOH | |
| 38 | B(OH)$_3$ | Oil |

EXAMPLE 39-41

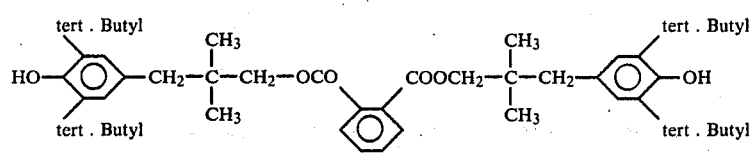

58.5 g (0.2 mol) of 3-(3,5-di-tert.butyl-4-hydroxyphenyl)-2,2-dimethylpropyl alcohol and 14.8 g (0.1 mol) of phthalic anhydride in 200 ml of toluene are heated under reflux for 1 hour. A pinch of p-toluenesulphonic acid is then added to the reaction solution and the mixture is heated for a further 2 hours under reflux under a water separator. After cooling, the reaction mixture is washed with water and concentrated completely under reduced pressure. The residue is recrystallised from dioxane. The phthalic acid di-[3-(3,5-di-tert.butyl-4-hydroxyphenyl)-2,2-dimethylpropyl] ester thus obtained melts at 198° C.

If, in this example, the phthalic anhydride is replaced by an equivalent quantity of one of the anhydrides of Table V which follows, an analogous procedure gives the 3-(3,5-di-tert.butyl-4-hydroxyphenyl)-2,2-dimethylpropyl esters having the melting points quoted.

TABLE V

| Example No. | Anhydride | Melting point of the reaction product |
|---|---|---|
| 40 | (phthalic anhydride structure) | 139° C. |
| 41 | CH$_3$—COOCO—CH$_3$ | 102° C. |

EXAMPLES 42-44

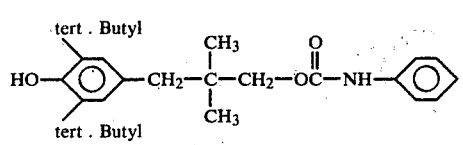

A solution of 7.3 g (0.025 mol) of 3-(3,5-di-tert.butyl-4-hydroxyphenyl)-2,2-dimethylpropanol in 25 ml of hexane is added dropwise at room temperature to a solution of 3.0 g (0.025 mol) of phenylisocyanate in 15 ml of hexane. The mixture is boiled under reflux for a further hour. The product is precipitated from the boiling solution after a short time. This gives N-phenylcarbamic acid 3-(3,5-di-tert.butyl-4-hydroxyphenyl)-2,2-dimethylpropyl ester, which, after recrystallisation from ligroin, melts at 162° C.

If, in this example, the phenylisocyanate is replaced by an equivalent quantity of one of the isocyanates of Table VI which follows, an otherwise identical procedure gives the N-substituted carbamic acid 3-(3,5-di-tert.butyl-4-hydroxyphenyl)-2,2-dimethylpropyl esters having the melting points quoted.

TABLE VI

| Example No. | Isocyanate | Melting point of the reaction product |
|---|---|---|
| 43 | ⟨◯⟩—NCS | 163° C. |
| 44 | OCN—(CH$_2$)$_6$—NCO | 190° C. |

EXAMPLE 45

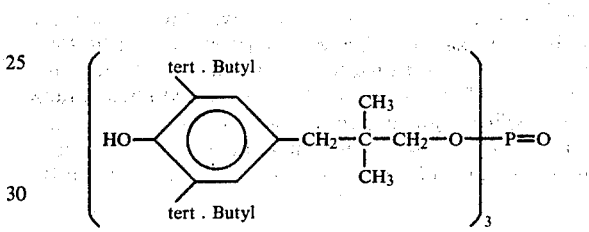

3.6 g (0.004 mol) of phosphorous acid tri-3-(3,5-di-tert.butyl-4-hydroxyphenyl)-2,2-dimethylpropyl ester (the product of Example 16) are initially introduced into 40 ml of dry ether. 2.0 g of cumene hydroperoxide are added dropwise at room temperature over the course of 10 minutes. After stirring for three hours, the mixture is evaporated and the residue is dried at 50° C. under a high vacuum, whereupon it crystallises slowly. The product is recrystallised from acetonitrile. This gives phosphoric acid tri-3-(3,5-di-tert.butyl-4-hydroxyphenyl)-2,2-dimethylpropyl ester of melting point 132° C.

EXAMPLE 46

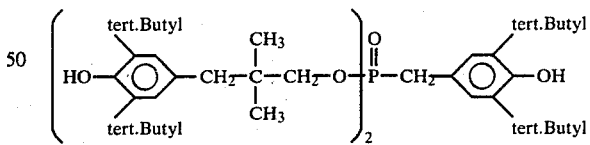

12.6 g (0.02 mol) of phosphorous acid di-3-(3,5-di-tert.butyl-4-hydroxyphenyl)-2,2-dimethylpropyl ester (the product of Example 26) and 5.2 g (0.02 mol) of 3,5-di-tert.butyl-4-hydroxybenzyldimethylamine are melted together at 100° C. The melt is treated with 0.05 g of lithium amide and heated to 120° C. and the reaction vessel is evacuated. After 2 hours, a further 0.05 g of lithium amide is added and the temperature is kept at 120° C. for a further 2 hours and the mixture is then cooled. The product, which has solidified as a glass, is purified by column chromatography by elution with a chloroform-methanol mixture (99:1) and is then recrystallised from acetonitrile. This gives 3,5-di-tert.butyl-4-hydroxybenzylphosphoric acid di-3-(3,5-ditert.butyl-4- hydroxyphenyl)-2,2-dimethylpropyl ester of melting point 124° C.

EXAMPLE 47

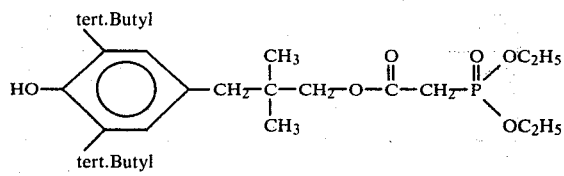

10.0 g (0.027 mol) of chloroacetic acid 3-(3,5-di-tert.butyl-4-hydroxyphenyl)-2,2-dimethylpropyl ester (the product of Example 37) and 25 g (160 mmols) of triethyl phosphite are boiled together for 14 hours under reflux (160° C.). After cooling, the excess triethyl phosphite is removed in a high vacuum at a slightly elevated temperature. The viscous oil which remains is diethylphosphorylacetic acid 3-(3,5-ditert.butyl-4-hydroxyphenyl)-

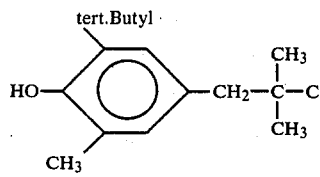

2,2-dimethylpropyl ester.

Analysis: Calculated—C 63.9, H 9.2, P 6.6; Found—C 64.2, H 9.3, P 6.6.

EXAMPLE 48

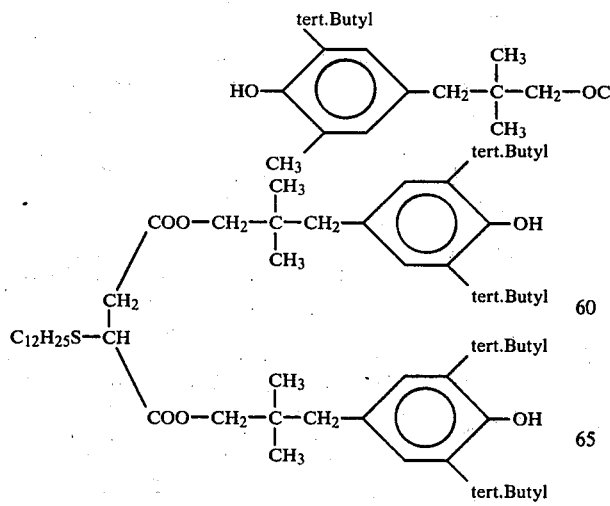

6.6 g (0.01 mol) of maleic acid di-3-(3,5-di-tert.-butyl-4-hydroxyphenyl)-2,2-dimethylpropyl ester (the product of Example 40), 2 g (0.01 mol) of dodecylmercaptan and 1 g of sodium acetate in 100 ml of ethanol are heated under reflux for 4 hours. 20 ml of water are then added and the mixture is slowly cooled. The precipitate which is thrown down is filtered off. After recrystallisation from a little ethanol, 2-dodecylmercaptosuccinic acid di-[3-(3,5-di-tert.butyl-4-hydroxyphenyl)-2,2-dimethylpropyl] ester melts at 87° C.

EXAMPLE 49

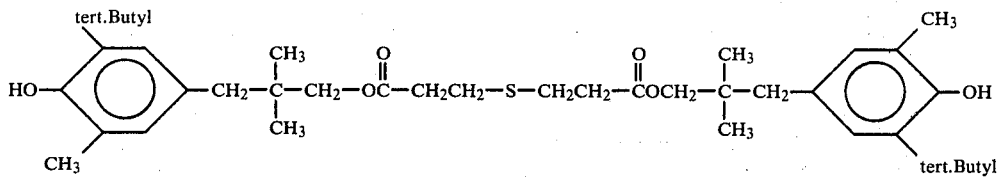

The procedure of Example 35 is repeated by reacting thiodipropionic acid with 3-(3-tert.butyl-4-hydroxy-5-methylphenyl)-2,2-dimethylpropyl alcohol in the presence of p-toluenesulphonic acid. This gives thiodipropionic acid di-[3-(3-tert.butyl-4-hydroxy-5-methylphenyl)-2,2-dimethylpropyl] ester of melting point 95° C.

EXAMPLE 50

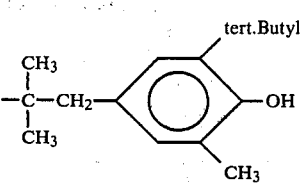

The procedure of Example 2 is repeated by reacting 3-(3-tert.butyl-4-hydroxy-5-methylphenyl)-2,2-dimethylpropyl alcohol with adipic acid dichloride in pyridine.

This gives adipic acid di-3-(3-tert.butyl-4-hydroxy-5-methylphenyl)-2,2-dimethylpropyl ester of melting point 113° C.

EXAMPLE 51

The procedure of Example 21 is repeated by reacting 3-(3-tert.butyl-4-hydroxy-5-methylphenyl)-2,2-dimethylpropyl alcohol with terephthalic acid dimethyl ester in the presence of lithium amide. This gives therephthalic acid di-3-(tert.butyl-4-hydroxy-5-methylphenyl)-2,2-dimethylpropyl ester of melting point 201° C.

EXAMPLE 52

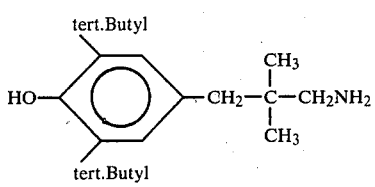

488 g (1.68 mols) of 3-(3,5-di-tert.butyl-4-hydroxyphenyl)-2,2-dimethylpropionaldehyde are dissolved in 3,000 ml of methanol, 700 g of liquid ammonia and 75 g of Raney nickel are added and hydrogenation is carried out in a shaking autoclave at an initial pressure of 100 bars, first at room temperature for 3 hours and then at 40°–50° C. for 8 hours. After cooling, the excess pressure is discharged and the catalyst is filtered off from the reaction mixture. The filtrate is concentrated to one half and 1,500 ml of water are added. The precipitate which is thrown down is recrystallised from hexane. After a further recrystallisation from acetonitrile, 3-(3,5-di-tert.butyl-4-hydroxyphenyl)-2,2-dimethylpropylamine melts at 106° C.

EXAMPLES 53–64

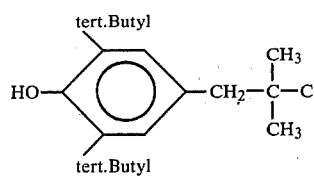

8.75 g (0.03 mol) of 3-(3,5-di-tert.butyl-4-hydroxyphenyl)-2,2-dimethylpropylamine and 3.2 g (0.03 mol) of triethylamine are initially introduced into 100 ml of absolute benzene. 2.75 g (0.015 mol) of adipic acid chloride, dissolved in 10 ml of absolute benzene, are added dropwise at room temperature over the course of 10 minutes. The mixture is then boiled under reflux for 3 hours, while stirring. The reaction mixture is then cooled, the precipitate which has formed is filtered off, and the solution is twice washed with 10% strength alcohol and is then evaporated. After recrystallisation from toluene, adipic acid di-[3-(3,5-di-tert.butyl-4-hydroxyphenyl)-2,2-dimethylpropyl]-amide melts at 188° C.

If, in this example, the adipic acid dichloride is replaced by an acid chloride of Table VII which follows, using the quoted amount, which is equivalent to the 3-(3,5-di-tert. butyl-4-hydroxyphenyl)-2,2-dimethylpropylamine employed, an otherwise identical procedure gives the 3-(3,5-di-tert.butyl-4-hydroxyphenyl)-2,2-dimethylpropylamides having the melting points quoted. In the case of Examples 63 and 64, the monoamide or di-amide of the dicyanuric or monocyanuric chloride respectively is formed.

TABLE VII

| Example No. | Acid chloride | Equimolecular quantity | Melting point of the reaction product |
|---|---|---|---|
| 54 | C₁₇H₃₅COCl | 1 | 67° C. |
| 55 | ![COCl-phenyl] C₆H₅-COCl | ½ | 214° C. |
| 56 | C₂H₅OCOCl | 1 | 70° C. |
| 57 | C₁₈H₃₇OCOCl | 1 | 58° C. |
| 58 | (CH₃)₃C—CH₂—C(CH₃)₂—C₆H₄—OCOCl | 1 | 112° C. |
| 59 | ClCOO—(CH₂)₆—OCOCl | ½ | 140° C. |
| 60 | (C₂H₅)₂NCOCl | 1 | 116° C. |
| 61 | (C₂H₅O)₂P(O)Cl | 1 | 94° C. |
| 62 | (C₂H₅O)₂P(S)Cl | 1 | Oil |
| 63 | 2,4,6-trichloro-s-triazine (monoamide) | 1 | 168° C. |
| 64 | cyanuric chloride (diamide) | ½ | 212° C. |

EXAMPLES 65–67

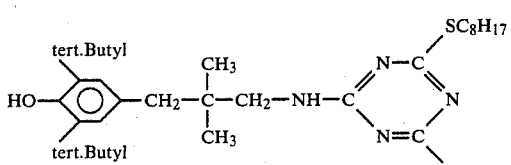

10 g (0.023 mol) of 1,3-dichloro-5-[3,5-di-tert. butyl-4-hydroxyphenyl)-2,2-dimethylpropylamino]-s-triazine (the product of Example 63) and 6.74 g (0.046 mol) of octylmercaptan are initially introduced at room temperature into 100 ml of acetone. 1.84 g (0.046 mol) of sodium hydroxide, dissolved in 2 ml of water, are now added dropwise while stirring, over the course of 3 minutes. The mixture is then stirred under reflux for a further 3 hours, insoluble matter is filtered off and the filtrate is concentrated to dryness. The oil which remains can be completely purified through a silica gel column using toluene as the migrating agent. This gives, as this substance, 1,3-dioctylmercapto-5-[3-(3,5-di-tert- .butyl-4-hydroxyphenyl)-2,2-dimethylpropylamino]-s-triazine.

If, in this example, the octylmercaptan is replaced by thiophenol or tert.octylphenol, an otherwise identical procedure gives the corresponding 3-(3,5-di-tert.butyl-4-hydroxyphenyl)-2,2-dimethylpropylamino-s-triazines having the melting points quoted in Table VIII.

TABLE VIII

| Example No. | Reagent | Melting point of the reaction product |
|---|---|---|
| 66 | ⟨O⟩—SH | 142° C. |
| 67 | CH₃—C(CH₃)₂—CH₂—C(CH₃)₂—⟨O⟩—OH | 166° C. |

EXAMPLE 68

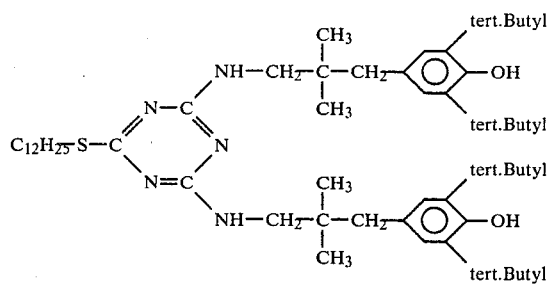

10.0 g (0.014 mol) of 1-chloro-3,5-di-[3-(3,5-di-tert.butyl-4-hydroxyphenyl)-2,2-dimethylpropylamino]-s-triazine (the product of Example 64) and 2.91 g (0.044 mol) of dodecylmercaptan are initially introduced into 50 ml of acetone and 0.58 g (0.0144 mol) of sodium hydroxide, dissolved in 1 ml of water, is added at room temperature. The mixture is then heated to the point of reflux and is stirred at this temperature for 5 hours. It is then cooled, insoluble matter is filtered off and the filtrate is concentrated completely. The residue is purified through a silica gel column using toluene:methanol (98:2) as the migrating agent. The 1-dodecylmercapto-3,5-di-[3-(3,5-di-tert.butyl-4-hydroxyphenyl)-2,2-dimethylpropylamino]-s-triazine obtained in this way is produced as a yellowish resin. (Stabiliser No. 68).

EXAMPLES 69–77

27.8 g (0.1 mol) of 4-(3,5-di-tert.butyl-4-hydroxyphenyl)-2-butanol are dissolved in 100 ml of pyridine. 10.1 g (0.05 mol) of terephthalic acid dichloride are added dropwise, over the course of 30 minutes, to the solution at room temperature. After the exothermic reaction has subsided, the mixture is heated for 2 hours to 80° C. It is poured into 500 ml of ice water and the resulting emulsion is acidified. The product which is precipitated is extracted with chloroform and the chloroform solution is evaporated. Crystallisation from dioxane gives terephthalic acid di-4-(3,5-di-tert.butyl-4-hydroxyphenyl)-2-butyl ester of melting point 154° C.

If, in this example, the terephthalic acid dichloride is replaced by one of the acid chlorides of Table IX which follows, using a quantity equivalent to the 4-(3,5-di-tert- .butyl-4-hydroxyphenyl)-2-butanol employed, an otherwise identical procedure gives the corresponding 4-(3,5-di-tert.butyl-4-hydroxyphenyl)-2-butyl esters.

TABLE IX

| Example No. | Acid chloride | Product |
|---|---|---|
| 70 | ClCO—(CH₂)₄—COCl | viscous oil |
| 71 | C₁₇H₃₅COCl | oil |
| 72 | ⟨O⟩—COCl | melting point 71° C. |
| 73 | tert.Butyl—⟨O⟩—COCl | resin |
| 74 | ClCO—⟨O⟩—⟨O⟩—COCl | resin |
| 75 | ClCO—⟨O⟩(COCl)—COCl | brittle resin |
| 76 | ClCOCH₂CH₂—S—CH₂CH₂COCl | oil |
| 77 | HO—⟨O⟩(tert.Butyl)(tert.Butyl)—CH₂CH₂COCl | oil |

EXAMPLES 78–81

If, in Example 2, the adipic acid dichloride is replaced by an acid chloride of Table X which follows, using the quantity quoted, which is equivalent to the 3-(3,5-di-tert.butyl-4-hydroxyphenyl)-2,2-dimethylpropanol employed, an otherwise identical procedure gives the 3-(3,5-di-tert.butyl-4-hydroxyphenyl)-2,2-dimethylpropyl esters having the melting points quoted.

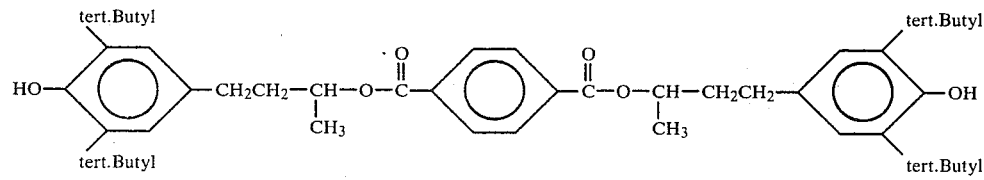

TABLE X

| Example No. | Acid chloride | Equi-molecular quantity | Melting point of the reaction product |
|---|---|---|---|
| 78 | (benzene-1,3-dicarbonyl dichloride) | ½ | viscous oil |
| 79 | C₂H₅OCOCl | 1 | 96° C. |
| 80 | (thiophene-2,5-dicarbonyl dichloride) | ½ | 158° C. |
| 81 | S=C(Cl)₂ (thiophosgene) | ½ | 168° C. |

EXAMPLE 82

If, in Example 21, the terephthalic acid dimethyl ester is replaced by one of the esters of Table XI which follows, using a quantity equivalent to the 3-(3,5-di-tert.butyl-4-hydroxyphenyl)-2,2-dimethylpropanol employed, an otherwise identical procedure gives the 3-(3,5-di-tert.butyl-4-hydroxyphenyl)-2,2-dimethylpropyl esters having the melting points quoted.

TABLE XI

| Example No. | Ester | Melting point of the reaction product |
|---|---|---|
| 82 | CH₃OCOCOOCH₃ | 176° C. |

EXAMPLES 83–84

If, in Example 35, the thiodiglycollic acid is replaced by one of the acids of Table XII which follows, using a quantity equivalent to the 3-(3,5-di-tert.butyl-4-hydroxyphenyl)-2,2-dimethylpropyl alcohol employed, an analogous procedure gives the 3-(3,5-di-tert.butyl-4-hydroxyphenyl)-2,2-dimethylpropyl esters having the melting points quoted.

TABLE XII

| Example No. | Acid | Melting point of the reaction product |
|---|---|---|
| 83 | HOOC—(CH₂)₈—COOH | 186° C. |
| 84 | Cyclohexanecarboxylic acid | 100° C. |

EXAMPLE 85

If, in Example 42, the phenylisocyanate is replaced by an equivalent quantity of toluylene-2,4-diisocyanate, an otherwise identical procedure gives toluylene-2,4-dicarbamic acid di-3-(3,5-di-tert.butyl-4-hydroxyphenyl)-2,2-dimethylpropyl ester of melting point 163° C.

EXAMPLES 86–90

If, in Example 48, the dodecylmercaptan is replaced by one of the thiol compounds of Table XIII which follows, an analogous procedure gives the 2-mercapto-substituted succinic acid di-[3-(3,5-di-tert.butyl-4-hydroxyphenyl)-2,2-dimethylpropyl] esters having the melting points quoted.

TABLE XIII

| Example No. | Thiol compound | Equi-molecular quantity | Melting point of the reaction product |
|---|---|---|---|
| 86 | HO—CH₂CH₂—SH | 1 | 156° C. |
| 87 | C₈H₁₇—SH | 1 | 126° C. |
| 88 | H₂S (passed in) | ½ | Resin |
| 89 | HS—CH₂CH₂—SH | ½ | 127° C. |
| 90 | HS—CH₂—COOC₁₈H₃₇ | 1 | 66° C. |

EXAMPLE 91

If, in Example 35, the 3-(3,5-di-tert.butyl-4-hydroxyphenyl)-2,2-dimethylpropyl alcohol is replaced by an equivalent quantity of 3-(3-tert.butyl-4-hydroxy-5-methylphenyl)-2,2-dimethylpropyl alcohol and the same procedure is followed in other respects, thiodiglycollic acid di-[3-(3-tert.butyl-4-hydroxy-5-methylphenyl)-2,2-dimethylpropyl] ester of melting point 63° C. is obtained.

EXAMPLE 92

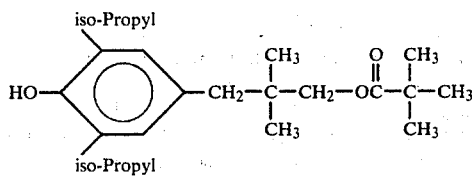

26.4 g (0.1 mol) of 3-(3,5-diisopropyl-4-hydroxyphenyl)-2,2-dimethylpropanol are dissolved in 100 ml of pyridine. 12.0 g (0.1 mol) of pivalic acid chloride are added dropwise to the solution over the course of 30 minutes at room temperature. After the strongly exothermic reaction has subsided, the mixture is heated to 80° C. for a further 2 hours. It is poured into 500 ml of ice water and the resulting emulsion is acidified, whereupon the product crystallises. After being filtered off and dried, the product is recrystallised from hexane. This gives pivalic acid 3-(3,5-diisopropyl-4-hydroxyphenyl)-2,2-dimethylpropyl ester of melting point 109° C.

EXAMPLE 93

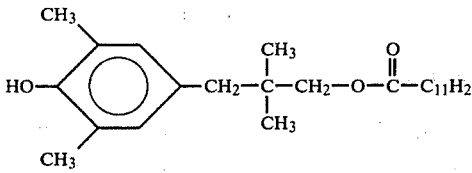

20.8 g (0.1 mol) of 3-(3,5-dimethyl-4-hydroxyphenyl)-2,2-dimethylpropanol are dissolved in 100 ml of pyridine. 21.8 g (0.1 mol) of lauric acid chloride are added dropwise to the solution over the course of 30 minutes at room temperature. After the strongly exothermic reaction has subsided, the mixture is heated to 80° C. for a further 2 hours. It is poured into 500 ml of ice water and the resulting emulsion is acidified and then extracted with ether. After evaporating the ether, lauric acid 3-(3,5-dimethyl-4-hydroxyphenyl)-2,2-dimethylpropyl ester is left as a residue and can be distilled. Boiling point 194°–198° C. at 0.01 mm.

EXAMPLE 94

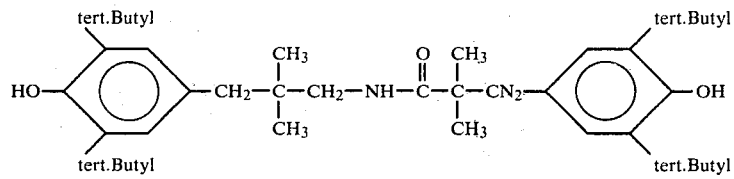

8.75 g (0.03 mol) of 3-(3,5-di-tert.butyl-4-hydroxyphenyl)-2,2-dimethylpropylamine and 3.2 g (0.03 mol) of triethylamine are initially introduced into 100 ml of absolute benzene. 9.7 g (0.03 mol) of 3-(3,5-di-tert.butyl-4-hydroxyphenyl-2,2-dimethylpropionyl chloride, dissolved in 20 ml of absolute benzene, are added dropwise at room temperature. The mixture is then boiled under reflux, while stirring, for 3 hours. The reaction mixture is cooled, the precipitate is filtered off and the solution is twice washed with water and then evaporated. The residue is recrystallised from acetonitrile. This gives 3-(3,5-di-tert.butyl-4-hydroxyphenyl)-2,2-dimethyl-propionic acid 3-(3,5-di-tert. butyl-4-hydroxyphenyl)-2,2-dimethylpropylamide of melting point 146° C.

EXAMPLES 96-97

If, in Example 68, the dodecylmercaptan is replaced by thiophenol or morpholine, an otherwise identical procedure gives the 1-substituted 3,5-di-[3-(3,5-di-tert-.butyl-4-hydroxyphenyl)-2,2-dimethylpropylamino]-s-triazines having the melting points given in Table XIV.

TABLE XIV

| Example No. | Reagent | Melting point of the product |
|---|---|---|
| 95 | HS—⟨O⟩ | 126° C. |
| 96 | O⟨CH₂—CH₂\CH₂—CH₂⟩NH | 120° C. |
| 97 | H₂N—CH₂—C(CH₃)(CH₃)—CH₂—⟨tert.Butyl / tert.Butyl⟩—OH | 140° C. |

EXAMPLE 98

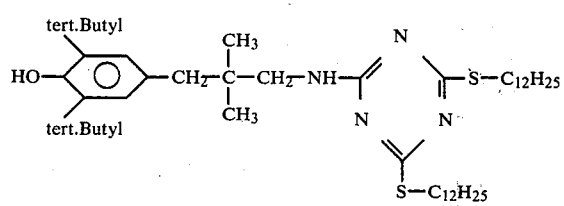

10 g (0.023 mol) of 1,3-dichloro-5-[3-(3,5-di-tert.butyl-4-hydroxyphenyl)-2,2-dimethylpropylamino]-s-triazine (the product of Example 63) and 9.3 g (0.046 mol) of dodecylmercaptan are initially introduced into 100 ml of acetone at room temperature. 1.84 g (0.046 mol) of sodium hydroxide, dissolved in 2 ml of water, are now added dropwise over the course of 3 minutes with stirring. The mixture is then stirred under reflux for a further 90 minutes, insoluble matter is filtered off and the filtrate is concentrated to dryness. The oil which remains can be completely purified through a silica gel column using toluene as the migrating agent. This gives 1,3-di-dodecylmercapto-5-[3-(3,5-di-tert.butyl-4-hydroxyphenyl)-2,2-dimethylpropylamino]-s-triazine.

EXAMPLE 99

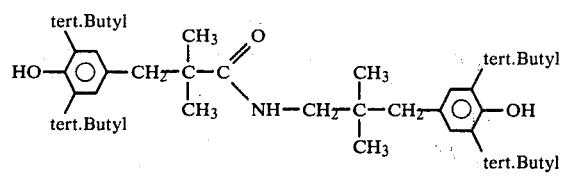

5.8 g (0.02 mol) of 3-(3,5-di-tert.butyl-4-hydroxyphenyl)-2,2-dimethylpropylamine and 2.02 g (0.02 mol) of triethylamine are initially introduced into 25 ml of absolute toluene. 7 g (0.0215 mol) of 3-(3,5-di-tert.butyl-4-hydroxyphenyl)-2,2-dimethylpropionic acid chloride, dissolved in 50 ml of absolute toluene, are added dropwise over the course of 10 minutes at room temperature. The mixture is then refluxed for 3 hours while stirring. The reaction mixture is then cooled, the precipitate which has formed is filtered off and the filtrate is concentrated completely. The residue is recrystallised, first from ligroin and then from acetonitrile. The resulting 3-(3,5-di-tert.butyl-4-hydroxyphenyl)-2,2-dimethylpropionic acid [3-(3,5-di-tert.butyl)-4-hydroxyphenyl)-2,2-dimethylpropyl]-amide melts at 144°-146° C.

EXAMPLE 100

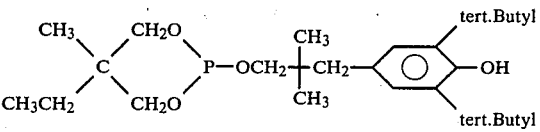

23.1 g (0.12 mol) of 3-(3,5-di-tert.butyl-4-hydroxyphenyl)-2,2-dimethylpropanol and 35.1 g (0.12 mol) of 1-methoxy-4-ethyl-4-methyl-2,6-dioxaphosphorane are initially taken and are warmed to an internal temperature of 110° C. 0.6 g (0.026 mol) of lithium amide are then added. The external temperature is now raised and is kept at 130° C. for 3 hours, during which time ethanol distils off. (Internal temperature 125° C.).

The internal temperature is then raised: 130° C. for 2 hours, 140° C. for 1½ hours and 145°-150° C. for 30 minutes. In the course thereof 4.2 g of ethanol distil off and a white precipitate is formed. On cooling, the reaction mixture crystallises out. It is recrystallised, first from hexane and then from acetonitrile. The 4-ethyl-4-methyl-1-[2,2-dimethyl-3-(3,5-di-tert.butyl-4-hydroxyphenyl)-propoxy]-2,6-dioxa-phosphorane obtained in this way melts at 100°-101° C.

EXAMPLE 101

100 parts of polypropylene (melt index 3.2 g/10 minutes, 230°/2,160 g) are intensively mixed for 10 minutes in a shaking apparatus with 0.2 part of an additive listed in Table XV which follows. The resulting mixture is kneaded for 10 minutes at 200° C. in a Brabender plastograph and the mass obtained in this way is subsequently pressed in a sheet press at 260° C. platen temperature to give 1 mm thick sheets, from which strips 1 cm wide and 17 cm long are punched.

The activity of the additives added to the test strips is tested by heat ageing in a circulating air oven at 135° C. and 149° C. an additive-free test strip serving for comparison. 3 test strips of each formulation are employed. The end point is defined as the incipient, easily visible crumbling of the test strip.

TABLE XV

| Stabiliser Example No. | Days to incipient decomposition | |
|---|---|---|
| | 149° C. | 135° C. |
| without additive | <1 | ~3 |
| 4 | 4 | 86 |
| 16 | 9 | 76 |
| 17 | 6 | 69 |
| 25 | 4 | 69 |
| 27 | 18 | 73 |
| 29 | 49 | 130 |
| 30 | 14 | 58 |
| 35 | 9 | 56 |
| 36 | 35 | 115 |
| 39 | 4 | 49 |
| 40 | 4 | 48 |
| 44 | 4 | 37 |
| 45 | 9 | 120 |
| 46 | 20 | 119 |
| 48 | 22 | 98 |
| 49 | 45 | 124 |
| 50 | 6 | 44 |
| 53 | 18 | 118 |
| 64 | 8 | 31 |
| 66 | 4 | 74 |
| 68 | 27 | 99 |
| 69 | 19 | 105 |
| 70 | 17 | 80 |
| 71 | 8 | 43 |
| 74 | 14 | 58 |
| 75 | 35 | 153 |
| 76 | 30 | 87 |
| 77 | 5 | 31 |
| 80 | 7 | 91 |
| 81 | 13 | 58 |
| 82 | 4 | 54 |
| 83 | 8 | 75 |
| 85 | 18 | 82 |
| 86 | 26 | 76 |
| 87 | 37 | 116 |
| 88 | 35 | 117 |
| 90 | 25 | 133 |
| 91 | 25 | 74 |
| 95 | 20 | 71 |
| 96 | 16 | 70 |
| 98 | 14 | 122 |
| 99 | 5 | 40 |
| 100 | 9 | 27 |

EXAMPLE 102

100 parts of polypropylene (melt index 3.2 g/10 minutes, 230° C./2,160 g) are intensively mixed for 10 minutes in a shaking apparatus with 0.1 part of an additive listed in Table XVI which follows and with 0.3 part of dilauryl thiodipropionate.

The resulting mixture is kneaded for 10 minutes in a Brabender plastograph at 200° C. and the mass obtained in this way is subsequently pressed in a sheet press at 260° C. platen temperature to give 1 mm thick sheets, from which strips 1 cm wide and 17 cm long are punched.

The activity of the additives added to the test strips is tested by heat ageing in a circulating air oven at 135° C. and 149° C., using for comparison a test strip which contains only 0.3 part of dilauryl thiodipropionate. For this purpose, three test strips of each formulation are employed. The end point is defined as the incipient, easily visible decomposition of the test strip.

TABLE XVI

| Stabiliser Example No. | Days to incipient decomposition | |
|---|---|---|
| | 149° C. | 135° C. |
| without additive | 5 | 11 |
| 2 | 24 | 122 |
| 3 | 10 | 59 |
| 4 | 28 | 135 |
| 7 | 20 | 79 |
| 9 | 20 | 87 |
| 11 | 16 | 64 |
| 16 | 52 | 157 |
| 17 | 48 | 131 |
| 18 | 14 | 37 |
| 21 | 28 | 132 |
| 25 | 48 | 149 |
| 26 | 10 | 59 |
| 29 | 27 | 87 |
| 30 | 16 | 78 |
| 35 | 32 | 122 |
| 36 | 41 | 122 |
| 39 | 19 | 76 |
| 40 | 28 | 104 |
| 44 | 32 | 100 |
| 45 | 22 | 112 |
| 48 | 36 | 118 |
| 50 | 25 | 83 |
| 51 | 29 | 85 |
| 53 | 29 | 114 |
| 54 | 19 | 69 |
| 55 | 22 | 98 |
| 59 | 28 | 98 |
| 64 | 16 | 67 |
| 65 | 31 | 120 |
| 66 | 21 | 84 |
| 67 | 20 | 77 |
| 68 | 20 | 94 |
| 69 | 35 | 147 |
| 70 | 31 | 129 |
| 71 | 19 | 71 |
| 74 | 35 | 132 |
| 75 | 45 | 164 |
| 76 | 42 | 133 |
| 77 | 12 | 47 |
| 80 | 23 | 104 |
| 82 | 22 | 67 |
| 83 | 26 | 97 |
| 85 | 23 | 96 |
| 86 | 27 | 76 |
| 87 | 40 | 116 |
| 88 | 35 | 124 |
| 90 | 41 | 146 |
| 91 | 31 | 93 |
| 95 | 25 | 71 |
| 96 | 18 | 74 |
| 98 | 30 | 147 |
| 99 | 14 | 53 |
| 100 | 16 | |

EXAMPLE 103

The colour stability of the test strips described in Example 101 was also tested, as follows:
 (a) After incorporation (Table XVII, column 2)
 (b) After 500 hours exposure in a Xenotest apparatus of Messrs. Hanau (Table XVII, column 3)
 (c) After a 1-week treatment with boiling water (Table XVII, column 4).

For Table XVII an empirical colour scale was used in which 5 denotes absence of colour, 4 denotes a slight discolouration which is just perceptible, and 3, 2, 1 and <1 denote successively greater discolouration.

TABLE XVII

| Stabiliser Example No. | Colour assessment according to scale, 1-5 | | |
|---|---|---|---|
| | After incorporation | After exposure | Boiling water for 1 week |
| 4 | 5 | 5 | 5 |
| 16 | 5 | 5 | 5 |
| 17 | 4-5 | 5 | 4-5 |
| 25 | 4-5 | 5 | 4-5 |
| 27 | 5 | 5 | 4-5 |
| 29 | 5 | 5 | 5 |
| 30 | 5 | 5 | 4-5 |
| 35 | 4-5 | 5 | 4-5 |
| 36 | 5 | 5 | 5 |
| 39 | 4-5 | 5 | 4-5 |
| 40 | 4-5 | 5 | 4-5 |
| 44 | 4-5 | 5 | 4-5 |
| 45 | 4-5 | 5 | 4-5 |
| 46 | 4-5 | 5 | 4-5 |
| 48 | 5 | 5 | 5 |
| 49 | 4-5 | 5 | 5 |
| 50 | 4-5 | 5 | 5 |
| 53 | 4 | 5 | 4 |
| 64 | 4-5 | 5 | 4-5 |
| 69 | 4 | 5 | 4-5 |
| 70 | 4-5 | 5 | 4-5 |
| 71 | 4-5 | 5 | 4-5 |
| 74 | 4-5 | 5 | 4-5 |
| 75 | 4-5 | 5 | 4-5 |
| 76 | 4-5 | 5 | 4-5 |
| 77 | 4-5 | 5 | 4 |
| 80 | 5 | 4-5 | 4-5 |
| 81 | 5 | 5 | 4-5 |
| 82 | 4-5 | 5 | 4-5 |
| 83 | 5 | 5 | 4-5 |
| 85 | 4-5 | 4-5 | 4 |
| 86 | 4-5 | 5 | 4-5 |
| 87 | 4-5 | 5 | 4-5 |
| 88 | 4-5 | 5 | 4-5 |
| 90 | 4-5 | 5 | 4-5 |
| 91 | 4-5 | 5 | 5 |
| 95 | 4-5 | 4 | 4-5 |
| 98 | 4-5 | 5 | 4-5 |
| 99 | 4-5 | 5 | 4-5 |
| 100 | 4 | 5 | 4-5 |

EXAMPLE 104

Shavings (chips) 25μ thick are cut with the aid of a microtome from the 1 mm thick test sheets described in Example 101. These chips are clamped between grids of stainless steel and the sample carriers thus obtained are suspended in a circulating air oven and are aged at 135° C. or 147° C. The end point is defined as the time after which, on gently tapping the grid, degraded polypropylene drops out in the form of a powder (checked 1-2x daily). The results are quoted in hours (Table XVIII).

TABLE XVIII

| Stabiliser Example No. | Hours to incipient decomposition | |
|---|---|---|
| | 147° C. | 135° C. |
| without additive | 1 | 5 |
| 29 | 100 | 300 |
| 36 | 140 | 310 |
| 48 | 90 | 330 |
| 49 | 125 | 250 |
| 68 | 100 | 325 |
| 70 | 45 | 140 |
| 75 | 210 | 720 |
| 76 | 70 | 240 |
| 85 | 75 | 225 |
| 86 | 100 | 300 |
| 87 | 150 | 350 |
| 88 | 175 | 475 |
| 90 | 100 | 300 |
| 91 | 100 | 300 |
| 95 | 75 | 225 |

EXAMPLE 105

Shavings (chips) 25μ thick are cut with the aid of a microtome from the 1 mm thick test sheets described in Example 102. These chips are clamped between grids of stainless steel and the sample carriers thus obtained are suspended in a circulating air oven and are aged at 135° C. or 147° C. The end point is defined as the time after which, on gently tapping the grid, degraded polypropylene drops out in the form of a powder (checked 1-2x daily). The results are quoted in hours (Table XIX).

TABLE XIX

| Stabiliser Example No. | Hours to incipient decomposition | |
|---|---|---|
| | 147° C. | 135° C. |
| without additive | 10 | 20 |
| 16 | 70 | 240 |
| 29 | 100 | 300 |
| 35 | 70 | 210 |
| 36 | 140 | 310 |
| 45 | 100 | 275 |
| 48 | 90 | 330 |
| 53 | 90 | 320 |
| 68 | 75 | 225 |
| 69 | 90 | 310 |
| 70 | 70 | 260 |
| 74 | 70 | 280 |
| 75 | 210 | 720 |
| 76 | 70 | 240 |
| 85 | 100 | 300 |
| 86 | 100 | 300 |
| 87 | 175 | 500 |
| 88 | 175 | 475 |
| 90 | 150 | 350 |
| 91 | 125 | 350 |
| 95 | 100 | 300 |
| 98 | 125 | 325 |

EXAMPLE 106

Stabilisation of ABS

Unstabilised ABS powder is mixed with 0.7% of stabiliser 2. The mixture is compounded at 180° C. in a Buss Co-kneader and granulated. The granules are injection-moulded at 240° C. in a screw injection moulding machine (Ankerwerk Nürnberg/Ge) to give small sheets of size 50×55×2 mm. The small sheets thus obtained are aged for 30 minutes in a circulating air oven at 200° C. and their degree of yellowing is periodically assessed (yellowness index according to ASTM D 1925-63 T).

TABLE XX

| Stabiliser No. | 0 minutes | 15 minutes | 30 minutes |
|---|---|---|---|
| without stabiliser | 15.6 | 63.1 | 78.5 |
| 2 | 6.8 | 36.9 | 59.8 |

EXAMPLE 107

100 parts of polypropylene powder [melt index 20 (230° C., 2,160 g)] are mixed in a Brabender kneader at 200° C. with 0.2 part of an additive of the table which follows.

The homogenised mixture is withdrawn from the kneader and is pre-pressed into sheets 2–3 mm thick by means of a toggle press. The sheets are then processed in a sheet press at 260° C., first to give a thickness of 0.3 mm, and, in a subsequent operation, to give films 0.1 mm thick.

While avoiding cooling below 150° C., the films thus produced are heat-treated for 1 hour at 150° C. and are chilled in water at 15° C. directly afterwards. The films produced in this way have a homogeneous structure of fine spherulites. Punched-out test samples have an elongation of 800%.

The films are mounted on sample carriers and are exposed in the Xenotest 150 exposure apparatus. Pieces of film are withdrawn after varying times and each group of 5 test pieces is punched in the form of a tensile test bar and the residual elongation thereof is determined. The exposure time after which the elongation at break of the films has fallen to 50% of its value before exposure is taken as a measure of the protective action of the additives. The values obtained are listed in Table XXI:

TABLE XXI

| Additive | Hours of exposure until the elongation at break has fallen to 50% of its initial value |
| --- | --- |
| 2,6-di-tert.butyl-p-cresol | 650 |
| Stabiliser No. 1 | 1,010 |
| Stabiliser No. 35 | 1,100 |

EXAMPLE 108

Protection of polyacrylonitrile (PAN) from yellowing 0.5 part of stabiliser 1 are dissolved, together with 25 parts of PAN, in 75 parts of dimethylformamide (DMF) at 70° C. for 4 hours. In a visual comparison, the stabilised solution already displays a markedly lighter colour than a solution free from additive. Films approx. 500μ thick are drawn on a sheet of glass from these solutions and are dried for 10 minutes at 125° C.

A visual assessment of the degree of yellowing of the dried films is carried out on a white background with the following results:

TABLE XXII

| | Discolouration |
| --- | --- |
| Comparison colour free from additive | yellow |
| 0.5% of stabiliser 1 | white with a very faint tinge of yellow |

The same results are obtained if, instead of dimethylformamide, other solvents are used, such as, for example, ethylene carbonate-water mixture (80:20).

EXAMPLE 109

16 g of 2,2-dimethyl-3-(4-hydroxy-3,5-di-t.butylphenyl)-n-propylisocyanate, which can be prepared by known methods by reacting the corresponding amine with phosgene, are dissolved in 150 ml of ligroin and are reacted with 14.6 g of 2,2-dimethyl-3-(4-hydroxy-3,5-di-t.butylphenyl)-n-propylamine, dissolved in 150 ml of ligroin. After a few minutes, N,N'-di-[2,2-dimethyl-3-(4-hydroxy-3,5-di-t.butylphenyl)-n-propyl]urea begins to precipitate. The reaction is completed by heating the suspension under reflux for one hour, the reaction mixture is cooled and the urea is then isolated and washed with ligroin. The melting point is 270° C.

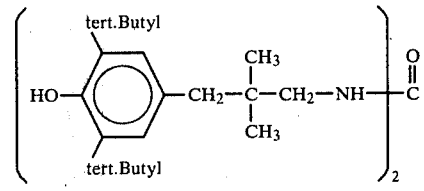

EXAMPLE 110

Reacting 2,2-dimethyl-3-(4-hydroxy-3,5-di.butylphenyl)-n-propylisocyanate with a molar quantity of 1,1,3,3-tetramethyl-n-butylamine using a procedure otherwise identical to that in Example 109 gives N-[2,2-dimethyl-3-(4-hydroxy-3,5-di.t.butylphenyl)-n-propyl]-N-(1,1,3,3-tetramethyl-n-butyl)urea having a melting point of 151° C.

What we claim is:
1. The compound

2. A composition of matter comprising polypropylene stabilized by the compound of claim 1.

* * * * *